United States Patent
Hoffmann et al.

(10) Patent No.: US 9,556,228 B2
(45) Date of Patent: Jan. 31, 2017

(54) MODIFIED APIDAECIN DERIVATIVES AS ANTIBIOTIC PEPTIDES

(71) Applicant: Universitaet Leipzig, Leipzig (DE)

(72) Inventors: Ralf Hoffmann, Grosspoesna (DE); Daniel Knappe, Leipzig (DE); Kai Hilpert, Weingarten (DE); Ralf Mikut, Karlsruhe (DE); Serge Ruden, Pforzheim (DE)

(73) Assignee: UNIVERSITAET LEIPZIG, Leipzig (DE)

( * ) Notice: Subject to any disclaimer, the term of this patent is extended or adjusted under 35 U.S.C. 154(b) by 0 days.

(21) Appl. No.: 14/346,624

(22) PCT Filed: Sep. 21, 2012

(86) PCT No.: PCT/EP2012/068620
§ 371 (c)(1),
(2) Date: Aug. 7, 2015

(87) PCT Pub. No.: WO2013/041663
PCT Pub. Date: Mar. 28, 2013

(65) Prior Publication Data
US 2015/0344524 A1    Dec. 3, 2015

(30) Foreign Application Priority Data

Sep. 22, 2011 (DE) .......... 10 2011 118 026

(51) Int. Cl.
*C07K 7/08* (2006.01)
*A61K 38/00* (2006.01)
*A61K 38/10* (2006.01)

(52) U.S. Cl.
CPC .......... *C07K 7/08* (2013.01); *A61K 38/00* (2013.01); *A61K 38/10* (2013.01)

(58) Field of Classification Search
CPC .................. A61K 38/00; C07K 7/08
See application file for complete search history.

(56) References Cited

U.S. PATENT DOCUMENTS 5,466,671 A * 11/1995 Tempst .......... A01N 37/46
514/2.8

FOREIGN PATENT DOCUMENTS

| DE | 10 2007 036128 | 2/2009 | |
| DE | CA 2751010 A1 * | 8/2010 | ....... C07K 14/43563 |
| WO | WO 95/23513 | 9/1995 | |
| WO | WO 2012/175532 | 12/2012 | |

OTHER PUBLICATIONS

Hilpert, Kai, et al.: "Screening and Characterization of Surface-Tethered Cationic Peptides for Antimicrobial Activity," Chemistry & Biology, vol. 16, pp. 58-69, 2009.
Taguchi, Seiichi, et al.: "Targeted Engineering of the Antibacterial Peptide Apidaecin, Based on an In Vivo Monitoring Assay System," Applied and Environmental Microbiology, vol. 75(5), pp. 1460-1464, 2009.
Xu, Peng, et al.: "Antimicrobial Peptide Evolution in the Asiatic Honey Bee *Apis cerana*," PLoS One, vol. 4(1), pp. 1-9, 2009.
International Search Report issued in International Patent Application PCT/EP2012/068620 on May 8, 2013.

* cited by examiner

*Primary Examiner* — Lianko Garyu
(74) *Attorney, Agent, or Firm* — Ballard Spahr LLP

(57) ABSTRACT

This invention relates to modified antibiotic peptides, particularly for use in medicine. The invention further relates to compositions and methods for destroying microorganisms, such as bacteria, viruses or fungi, and to methods for treating microbial infections. The object of the invention is to develop novel antibiotic peptides, particularly having enhanced antibiotic activity and an expanded spectrum of activity against other strains of bacteria, particularly gram-positive bacteria such as *Staphylococcus aureus*.
According to the invention, the object is attained in a first aspect by a peptide according to claim 1.

4 Claims, 3 Drawing Sheets

Fig. 1

Substituted Amino Acids

Figure 3:
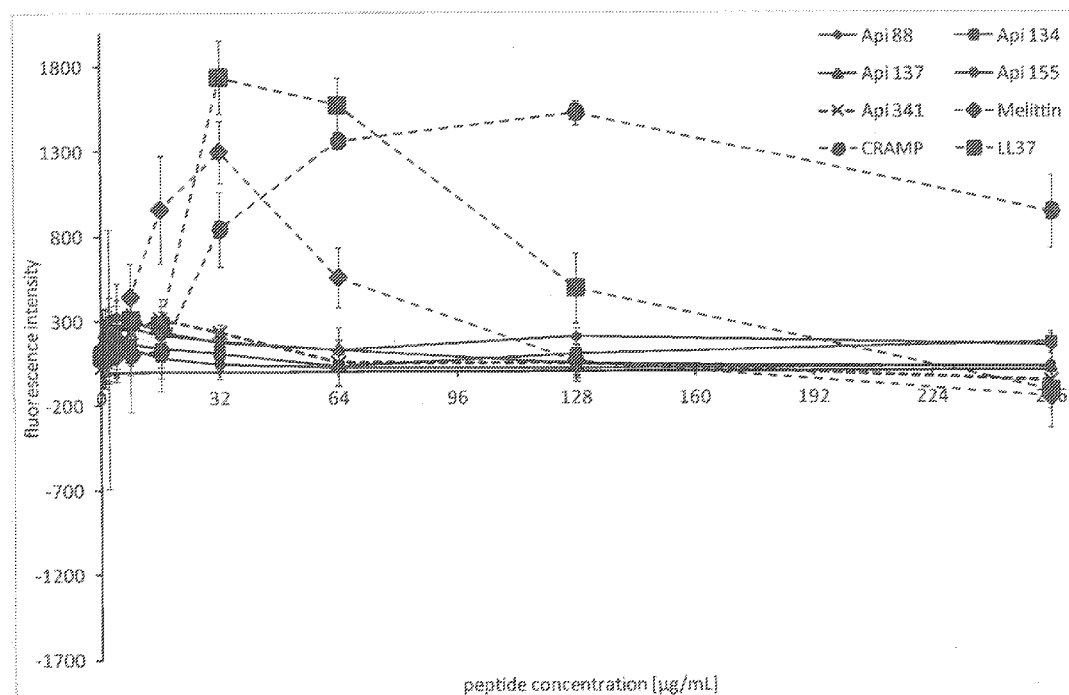

| Sequence | A | C | D | E | F | G | H | I | K | L | M | N | P | Q | R | S | T | V | W | Y |
|---|---|---|---|---|---|---|---|---|---|---|---|---|---|---|---|---|---|---|---|---|
| 1 G | 1,01 | 0,55 | 11,52 | 9,14 | 1,09 | | 1,03 | 1,01 | 0,27 | 0,73 | 1,05 | 1,25 | 0,67 | 1,55 | 0,61 | 1,78 | 1,68 | 1,05 | 0,66 | 0,76 |
| 2 N | 0,68 | 0,26 | 11,83 | 5,68 | 0,32 | 0,81 | 0,44 | 0,44 | 0,21 | 0,42 | 0,41 | | 0,62 | 0,72 | 0,17 | 0,64 | 0,53 | 0,57 | 0,25 | 0,54 |
| 3 N | 1,03 | 0,26 | 7,67 | 7,18 | 0,58 | 1,43 | 0,59 | 0,55 | 0,31 | 0,82 | 0,82 | | 0,57 | 0,88 | 0,29 | 0,69 | 0,82 | 0,64 | 0,53 | 1,07 |
| 4 R | 7,59 | 1,20 | >200 | >200 | 3,60 | 6,92 | 4,96 | 5,65 | 0,94 | 6,22 | 6,38 | 8,99 | 5,92 | 8,01 | | 6,38 | 7,18 | 10,77 | 8,27 | 12,49 |
| 5 P | 1,23 | 0,15 | >200 | >200 | 0,56 | 0,79 | 0,36 | 0,51 | 0,16 | 0,56 | 0,70 | 0,71 | | 0,94 | 0,14 | 0,67 | 0,56 | 0,52 | 0,31 | 0,58 |
| 6 V | 1,78 | 0,30 | 25,36 | >200 | 0,91 | 1,69 | 0,77 | 0,73 | 0,27 | 0,93 | 1,07 | 1,13 | 0,73 | 1,19 | 0,24 | 1,10 | 1,51 | | 0,55 | 0,83 |
| 7 Y | 7,20 | 0,29 | >200 | >200 | 1,45 | 4,73 | 1,88 | 2,68 | 0,36 | 1,95 | 4,03 | 3,89 | 3,22 | 2,91 | 0,40 | 3,76 | 3,76 | 4,09 | 1,69 | |
| 8 I | 2,12 | 0,23 | >200 | >200 | 0,94 | 1,56 | 0,73 | | 0,16 | 1,07 | 1,54 | 1,05 | 1,86 | 1,37 | 0,12 | 1,18 | 1,53 | 1,17 | 1,38 | 1,09 |
| 9 P | 3,57 | 0,19 | 63,87 | 31,37 | 0,79 | 1,26 | 0,82 | 1,15 | 0,31 | 1,28 | 1,64 | 1,23 | | 1,55 | 0,29 | 1,66 | 2,04 | 1,76 | 0,79 | 1,25 |
| 10 Q | 1,59 | 0,29 | 87,35 | >200 | 0,81 | 1,37 | 0,62 | 0,98 | 0,17 | 0,93 | 1,48 | 1,18 | 1,33 | | 0,17 | 1,22 | 1,42 | 1,42 | 1,17 | 1,25 |
| 11 P | 2,30 | 0,18 | 9,73 | 12,69 | 0,83 | 1,35 | 0,91 | 1,27 | 0,23 | 1,32 | 1,55 | 1,49 | | 1,36 | 0,20 | 1,36 | 1,23 | 1,28 | 0,83 | 1,21 |
| 12 R | 3,12 | 1,79 | 8,16 | 11,37 | 3,34 | 6,68 | 4,35 | 4,95 | 0,81 | 5,32 | 5,94 | 4,90 | 5,34 | 5,60 | | 7,25 | 6,33 | 6,51 | 4,21 | 6,06 |
| 13 P | 1,47 | 0,21 | 5,75 | 7,25 | 1,07 | 1,68 | 0,86 | 1,08 | 0,29 | 1,15 | 1,21 | 1,23 | | 1,31 | 0,21 | 1,34 | 1,29 | 1,37 | 1,15 | 1,29 |
| 14 P | 1,98 | 0,27 | 10,41 | 10,84 | 1,19 | 2,31 | 0,98 | 1,05 | 0,38 | 1,45 | 1,66 | 2,51 | | 2,26 | 0,51 | 2,10 | 2,41 | 1,88 | 1,40 | 1,91 |
| 15 H | 3,83 | 0,56 | 5,10 | 5,71 | 1,53 | 3,15 | | 2,28 | 0,58 | 2,29 | 2,15 | 2,54 | 2,61 | 2,71 | 0,52 | 2,57 | 3,03 | 2,39 | 2,60 | 1,96 |
| 16 P | 2,19 | 0,18 | 6,20 | 6,25 | 1,45 | 2,11 | 1,52 | 2,05 | 0,36 | 1,74 | 1,74 | 2,40 | | 2,30 | 0,40 | 1,92 | 2,29 | 2,31 | 1,07 | 1,78 |
| 17 R | 4,95 | 2,24 | 6,97 | 7,22 | 4,45 | 4,67 | 4,30 | 4,81 | 2,07 | 5,13 | 5,05 | 5,83 | 5,41 | 6,33 | 1,08 | 4,24 | | 4,13 | 3,13 | 3,96 |
| 18 L | 2,02 | 0,57 | 5,35 | 5,47 | 1,10 | 3,84 | 1,25 | 1,87 | 0,38 | | 1,47 | 2,80 | 3,14 | 2,22 | 0,35 | 2,12 | 2,01 | 1,83 | 1,11 | 1,44 |

| Sequence | A | C | D | E | F | G | H | I | K | L | M | N | P | Q | R | S | T | V | W | Y |
|---|---|---|---|---|---|---|---|---|---|---|---|---|---|---|---|---|---|---|---|---|
| 1G |   | X |   |   |   |   |   |   | X | X |   |   | X | X | X | X | X | X | X | X |
| 2N | X | X |   |   | X | X | X | X | X | X | X |   | X | X | X | X | X | X | X | X |
| 3N |   | X |   |   | X | X | X | X | X | X | X |   | X | X | X | X | X | X | X | X |
| 4R |   |   |   |   |   |   |   |   | X |   |   |   |   |   |   |   |   |   | X | X |
| 5P |   | X |   |   | X | X | X | X | X | X | X | X | X | X | X | X | X | X | X | X |
| 6V |   | X |   |   | X | X | X | X | X | X | X | X | X |   | X | X | X |   | X | X |
| 7Y |   | X |   |   |   |   | X | X | X | X | X |   |   |   | X |   |   |   | X | X |
| 8I |   | X |   |   | X | X | X |   | X | X | X |   |   |   | X |   |   |   | X | X |
| 9P |   | X |   |   | X | X | X | X | X | X | X |   |   |   | X |   |   |   | X | X |
| 10Q |   | X |   |   |   |   | X | X | X |   | X |   |   |   | X |   |   |   | X | X |
| 11P |   | X |   |   |   |   |   |   | X | X |   |   |   |   | X |   |   |   | X | X |
| 12R |   |   |   |   |   |   |   | X | X | X | X |   |   |   | X |   |   |   | X | X |
| 13P |   | X |   |   |   |   |   |   | X |   |   |   | X |   | X |   |   |   | X | X |
| 14P |   | X |   |   |   |   | X |   | X |   |   |   |   |   | X |   |   |   | X | X |
| 15H |   | X |   |   |   |   | X |   | X |   |   |   |   |   | X |   |   |   | X |   |
| 16P |   | X |   |   |   |   |   |   | X |   |   |   |   |   | X |   |   |   | X |   |
| 17R |   |   |   |   |   |   |   |   |   |   |   |   |   |   | X |   |   |   |   |   |
| 18L |   | X |   |   |   |   |   |   | X |   |   |   |   |   | X |   |   |   |   |   |

Substituted Amino Acids

Fig.2

SEQUENCE LISTING

```
<160> NUMBER OF SEQ ID NOS: 118

<210> SEQ ID NO 1
<211> LENGTH: 18
<212> TYPE: PRT
<213> ORGANISM: Apis mellifera

<400> SEQUENCE: 1

Gly Asn Asn Arg Pro Val Tyr Ile Pro Gln Pro Arg Pro Pro His Pro
1               5                   10                  15

Arg Ile

<210> SEQ ID NO 2
<211> LENGTH: 18
<212> TYPE: PRT
<213> ORGANISM: Apis mellifera

<400> SEQUENCE: 2

Gly Asn Asn Arg Pro Val Tyr Ile Pro Gln Pro Arg Pro Pro His Pro
1               5                   10                  15

Arg Leu

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (3)..(4)
<223> OTHER INFORMATION: Any naturally occurring amino acid
<220> FEATURE:
<221> NAME/KEY: MOD_RES
<222> LOCATION: (10)..(11)
<223> OTHER INFORMATION: Any naturally occurring amino acid

<400> SEQUENCE: 3

Xaa Asn Xaa Xaa Pro Val Tyr Ile Pro Xaa Xaa Arg Pro Pro His Pro
1               5                   10                  15

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
```

```
<221> NAME/KEY: MOD_RES
<222> LOCATION: (3)..(5)
<223> OTHER INFORMATION: Any naturally occurring amino acid

<400> SEQUENCE: 4

Xaa Pro Xaa Xaa Xaa Pro
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any naturally occurring amino acid

<400> SEQUENCE: 5

Pro Arg Pro Pro His Pro Arg Xaa
1               5

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any naturally occurring amino acid

<400> SEQUENCE: 6

Gly Asn Asn Arg Pro Xaa Tyr Ile Pro Gln Pro Arg Pro Pro His Pro
1               5                   10                  15

Arg

<210> SEQ ID NO 7
<211> LENGTH: 19
<212> TYPE: PRT
<213> ORGANISM: Drosophila melanogaster

<400> SEQUENCE: 7

Gly Lys Pro Arg Pro Tyr Ser Pro Arg Pro Thr Ser His Pro Arg Pro
1               5                   10                  15

Ile Arg Val

<210> SEQ ID NO 8
<211> LENGTH: 16
<212> TYPE: PRT
<213> ORGANISM: Myrmecia gulosa

<400> SEQUENCE: 8

Gly Arg Pro Asn Pro Val Asn Asn Lys Pro Thr Pro Tyr Pro His Leu
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 9

Gly Trp Asn Arg Pro Val Tyr Ile Pro Arg Pro Arg Arg Pro His Pro
1               5                   10                  15

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Trp Asn Arg Pro Val Tyr Ile Pro Arg Pro Arg Arg Pro His Pro
1               5                   10                  15

Arg Leu

<210> SEQ ID NO 11
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Trp Asn Arg Pro Val Tyr Ile Pro Arg Pro Arg Arg Pro His Pro
1               5                   10                  15

Arg Ile

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Trp Asn Arg Pro Val Tyr Ile Pro Gln Pro Arg Arg Pro His Pro
1               5                   10                  15

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Trp Asn Arg Pro Val Tyr Ile Pro Gln Pro Arg Arg Pro His Pro
1               5                   10                  15

Arg Leu

<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Trp Asn Arg Pro Val Tyr Ile Pro Gln Pro Arg Arg Pro His Pro
1               5                   10                  15

Arg Ile

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Trp Asn Arg Pro Val Tyr Ile Pro Gln Pro Arg Pro Pro His Pro
1               5                   10                  15

Arg Leu

<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Arg Asn Arg Pro Val Tyr Ile Pro Gln Pro Arg Pro Pro His Pro
1               5                   10                  15

Arg Leu

<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Asn Asn Arg Cys Val Tyr Ile Pro Gln Pro Arg Pro Pro His Pro
1               5                   10                  15

Arg Leu

<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Asn Asn Arg Arg Val Tyr Ile Pro Gln Pro Arg Pro Pro His Pro
1               5                   10                  15

Arg Leu

<210> SEQ ID NO 19
<211> LENGTH: 18
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 19

Gly Asn Asn Arg Pro Val Tyr Arg Pro Gln Pro Arg Pro Pro His Pro
1               5                   10                  15

Arg Leu

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Asn Asn Arg Pro Val Tyr Ile Pro Gln Pro Arg Arg Pro His Pro
1               5                   10                  15

Arg Leu

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Asn Asn Arg Pro Val Tyr Ile Pro Gln Pro Arg Pro Cys His Pro
1               5                   10                  15

Arg Leu

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Asn Asn Arg Pro Val Tyr Ile Pro Gln Pro Arg Pro Pro His Cys
1               5                   10                  15

Arg Leu

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Asn Asn Arg Pro Val Tyr Ile Pro Gln Pro Arg Pro Pro His Pro
1               5                   10                  15

Arg Arg

<210> SEQ ID NO 24
<211> LENGTH: 18
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 24

Gly Asn Asn Arg Pro Val Tyr Ile Pro Arg Pro Arg Arg Pro His Pro
1               5                   10                  15

Arg Leu

<210> SEQ ID NO 25
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn

<400> SEQUENCE: 25

Arg Trp Asn Arg Pro Val Tyr Ile Pro Arg Pro Arg Arg Pro His Pro
1               5                   10                  15

Arg Ile

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn

<400> SEQUENCE: 26

Arg Trp Asn Arg Pro Val Tyr Ile Pro Arg Pro Arg Arg Pro His Pro
1               5                   10                  15

Arg Leu

<210> SEQ ID NO 27
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (17)..(17)
<223> OTHER INFORMATION: Orn

<400> SEQUENCE: 27

Arg Trp Asn Arg Pro Val Tyr Ile Pro Arg Pro Arg Arg Pro His Pro
1               5                   10                  15

Arg Ile

<210> SEQ ID NO 28
<211> LENGTH: 18
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (17)..(17)
<223> OTHER INFORMATION: Orn

<400> SEQUENCE: 28

Arg Trp Asn Arg Pro Val Tyr Ile Pro Arg Pro Arg Arg Pro His Pro
1               5                   10                  15

Arg Leu

<210> SEQ ID NO 29
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Trp Asn Arg Pro Val Tyr Ile Pro Arg Pro Arg Arg Pro His Pro
1               5                   10                  15

Arg Cys

<210> SEQ ID NO 30
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Trp Asn Arg Pro Val Tyr Ile Pro Arg Pro Arg Arg Pro His Pro
1               5                   10                  15

Arg Cys

<210> SEQ ID NO 31
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Trp Asn Arg Pro Val Tyr Ile Pro Gln Pro Arg Arg Pro His Pro
1               5                   10                  15

Arg Cys

<210> SEQ ID NO 32
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 32

Gly Trp Asn Arg Pro Val Tyr Ile Pro Gln Pro Arg Arg Pro His Pro
1               5                   10                  15

Arg Cys

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Trp Asn Arg Pro Val Tyr Ile Pro Gln Pro Arg Pro Pro His Pro
1               5                   10                  15

Arg Cys

<210> SEQ ID NO 34
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Arg Asn Arg Pro Val Tyr Ile Pro Gln Pro Arg Pro Pro His Pro
1               5                   10                  15

Arg Cys

<210> SEQ ID NO 35
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Asn Asn Arg Arg Val Tyr Ile Pro Gln Pro Arg Pro Pro His Pro
1               5                   10                  15

Arg Cys

<210> SEQ ID NO 36
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Asn Asn Arg Pro Val Tyr Arg Pro Gln Pro Arg Pro Pro His Pro
1               5                   10                  15

Arg Cys

<210> SEQ ID NO 37
<211> LENGTH: 18
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 37

Gly Asn Asn Arg Pro Val Tyr Ile Pro Gln Pro Arg Arg Pro His Pro
1               5                   10                  15

Arg Cys

<210> SEQ ID NO 38
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Asn Asn Arg Pro Val Tyr Ile Pro Gln Pro Arg Pro Pro His Pro
1               5                   10                  15

Arg Cys

<210> SEQ ID NO 39
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Asn Asn Arg Pro Val Tyr Ile Pro Arg Pro Arg Arg Pro His Pro
1               5                   10                  15

Arg Cys

<210> SEQ ID NO 40
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn

<400> SEQUENCE: 40

Arg Trp Asn Arg Pro Val Tyr Ile Pro Arg Pro Arg Arg Pro His Pro
1               5                   10                  15

Arg Cys

<210> SEQ ID NO 41
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn
```

```
<400> SEQUENCE: 41

Arg Trp Asn Arg Pro Val Tyr Ile Pro Arg Pro Arg Arg Pro His Pro
1               5                   10                  15

Arg Cys

<210> SEQ ID NO 42
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (17)..(17)
<223> OTHER INFORMATION: Orn

<400> SEQUENCE: 42

Arg Trp Asn Arg Pro Val Tyr Ile Pro Arg Pro Arg Arg Pro His Pro
1               5                   10                  15

Arg Cys

<210> SEQ ID NO 43
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (17)..(17)
<223> OTHER INFORMATION: Orn

<400> SEQUENCE: 43

Arg Trp Asn Arg Pro Val Tyr Ile Pro Arg Pro Arg Arg Pro His
1               5                   10                  15

Pro Arg Cys

<210> SEQ ID NO 44
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn

<400> SEQUENCE: 44

Arg Asn Asn Arg Pro Val Tyr Ile Pro Arg Pro Arg Pro Pro His Pro
1               5                   10                  15

Arg Arg
```

-continued

```
<210> SEQ ID NO 45
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn

<400> SEQUENCE: 45

Arg Trp Asn Arg Pro Val Tyr Ile Pro Arg Pro Arg Pro Pro His Pro
1               5                   10                  15

Arg Leu

<210> SEQ ID NO 46
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn

<400> SEQUENCE: 46

Arg Asn Asn Arg Pro Val Tyr Ile Pro Arg Pro Arg Arg Pro His Pro
1               5                   10                  15

Arg Leu

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn

<400> SEQUENCE: 47

Arg Trp Asn Arg Pro Val Tyr Ile Pro Arg Pro Arg Pro His Pro
1               5                   10                  15

Arg Leu

<210> SEQ ID NO 48
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn

<400> SEQUENCE: 48

Arg Asn Asn Arg Pro Val Tyr Ile Pro Arg Pro Arg Arg Pro His Pro
1               5                   10                  15

Arg Leu
```

```
<210> SEQ ID NO 49
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn

<400> SEQUENCE: 49

Arg Trp Asn Arg Pro Val Tyr Ile Pro Arg Pro Arg Arg Pro His Pro
1               5                   10                  15

Arg Ile

<210> SEQ ID NO 50
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION

<400> SEQUENCE: 50

Gly Trp Asn Arg Pro Val Tyr Ile Pro Arg Pro Arg Arg Pro His Pro
1               5                   10                  15

Arg Leu

<210> SEQ ID NO 51
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION

<400> SEQUENCE: 51

Gly Trp Asn Arg Pro Val Tyr Ile Pro Arg Pro Arg Arg Pro His Pro
1               5                   10                  15

Arg Ile

<210> SEQ ID NO 52
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION

<400> SEQUENCE: 52

Gly Trp Asn Arg Pro Val Tyr Ile Pro Gln Pro Arg Arg Pro His Pro
1               5                   10                  15

Arg Leu
```

```
<210> SEQ ID NO 53
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION

<400> SEQUENCE: 53

Gly Trp Asn Arg Pro Val Tyr Ile Pro Gln Pro Arg Arg Pro His Pro
1               5                   10                  15

Arg Ile

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION

<400> SEQUENCE: 54

Gly Trp Asn Arg Pro Val Tyr Ile Pro Gln Pro Arg Pro Pro His Pro
1               5                   10                  15

Arg Leu

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION

<400> SEQUENCE: 55

Gly Arg Asn Arg Pro Val Tyr Ile Pro Gln Pro Arg Pro Pro His Pro
1               5                   10                  15

Arg Leu

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION
```

<400> SEQUENCE: 56

Gly Asn Asn Arg Cys Val Tyr Ile Pro Gln Pro Arg Pro Pro His Pro
1               5                   10                  15

Arg Leu

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION

<400> SEQUENCE: 57

Gly Asn Asn Arg Arg Val Tyr Ile Pro Gln Pro Arg Pro Pro His Pro
1               5                   10                  15

Arg Leu

<210> SEQ ID NO 58
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION

<400> SEQUENCE: 58

Gly Asn Asn Arg Pro Val Tyr Arg Pro Gln Pro Arg Pro Pro His Pro
1               5                   10                  15

Arg Leu

<210> SEQ ID NO 59
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION

<400> SEQUENCE: 59

Gly Asn Asn Arg Pro Val Tyr Ile Pro Gln Pro Arg Arg Pro His Pro
1               5                   10                  15

Arg Leu

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)

<223> OTHER INFORMATION: AMIDATION

<400> SEQUENCE: 60

Gly Asn Asn Arg Pro Val Tyr Ile Pro Gln Pro Arg Pro Cys His Pro
1               5                   10                  15

Arg Leu

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION

<400> SEQUENCE: 61

Gly Asn Asn Arg Pro Val Tyr Ile Pro Gln Pro Arg Pro Pro His Cys
1               5                   10                  15

Arg Leu

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Arginine amide
<220> FEATURE:
<221> NAME/KEY: MOD_RES
<222> LOCATION: (18)..(18)
<223> OTHER INFORMATION: AMIDATION

<400> SEQUENCE: 62

Gly Asn Asn Arg Pro Val Tyr Ile Pro Gln Pro Arg Pro Pro His Pro
1               5                   10                  15

Arg Arg

<210> SEQ ID NO 63
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION

<400> SEQUENCE: 63

Gly Trp Asn Arg Pro Val Tyr Ile Pro Gln Pro Arg Arg Pro His Pro
1               5                   10                  15

Arg Leu

<210> SEQ ID NO 64
<211> LENGTH: 18
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION

<400> SEQUENCE: 64

Gly Asn Asn Arg Pro Val Tyr Ile Pro Arg Pro Arg Arg Pro His Pro
1               5                   10                  15

Arg Leu

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (18)..(18)
<223> OTHER INFORMATION: AMIDATION

<400> SEQUENCE: 65

Arg Trp Asn Arg Pro Val Tyr Ile Pro Arg Pro Arg Arg Pro His Pro
1               5                   10                  15

Arg Ile

<210> SEQ ID NO 66
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (18)..(18)
<223> OTHER INFORMATION: AMIDATION

<400> SEQUENCE: 66

Arg Trp Asn Arg Pro Val Tyr Ile Pro Arg Pro Arg Arg Pro His Pro
1               5                   10                  15

Arg Leu

<210> SEQ ID NO 67
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (17)..(17)
<223> OTHER INFORMATION: Orn
<220> FEATURE:
```

```
<221> NAME/KEY: MOD_RES
<222> LOCATION: (18)..(18)
<223> OTHER INFORMATION: AMIDATION

<400> SEQUENCE: 67

Arg Trp Asn Arg Pro Val Tyr Ile Pro Arg Pro Arg Arg Pro His Pro
1               5                   10                  15

Arg Ile

<210> SEQ ID NO 68
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (17)..(17)
<223> OTHER INFORMATION: Orn
<220> FEATURE:
<221> NAME/KEY: MOD_RES
<222> LOCATION: (18)..(18)
<223> OTHER INFORMATION: AMIDATION

<400> SEQUENCE: 68

Arg Trp Asn Arg Pro Val Tyr Ile Pro Arg Pro Arg Arg Pro His Pro
1               5                   10                  15

Arg Leu

<210> SEQ ID NO 69
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION

<400> SEQUENCE: 69

Gly Trp Asn Arg Pro Val Tyr Ile Pro Arg Pro Arg Arg Pro His Pro
1               5                   10                  15

Arg Cys

<210> SEQ ID NO 70
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION

<400> SEQUENCE: 70

Gly Trp Asn Arg Pro Val Tyr Ile Pro Arg Pro Arg Arg Pro His Pro
1               5                   10                  15

Arg Cys
```

```
<210> SEQ ID NO 71
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION

<400> SEQUENCE: 71

Gly Trp Asn Arg Pro Val Tyr Ile Pro Gln Pro Arg Arg Pro His Pro
1               5                   10                  15

Arg Cys

<210> SEQ ID NO 72
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION

<400> SEQUENCE: 72

Gly Trp Asn Arg Pro Val Tyr Ile Pro Gln Pro Arg Arg Pro His Pro
1               5                   10                  15

Arg Cys

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION

<400> SEQUENCE: 73

Gly Trp Asn Arg Pro Val Tyr Ile Pro Gln Pro Arg Pro Pro His Pro
1               5                   10                  15

Arg Cys

<210> SEQ ID NO 74
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION

<400> SEQUENCE: 74

Gly Arg Asn Arg Pro Val Tyr Ile Pro Gln Pro Arg Pro Pro His Pro
1               5                   10                  15

Arg Cys
```

<210> SEQ ID NO 75
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION

<400> SEQUENCE: 75

Gly Asn Asn Arg Arg Val Tyr Ile Pro Gln Pro Arg Pro Pro His Pro
1               5                   10                  15

Arg Cys

<210> SEQ ID NO 76
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION

<400> SEQUENCE: 76

Gly Asn Asn Arg Pro Val Tyr Arg Pro Gln Pro Arg Pro Pro His Pro
1               5                   10                  15

Arg Cys

<210> SEQ ID NO 77
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION

<400> SEQUENCE: 77

Gly Asn Asn Arg Pro Val Tyr Ile Pro Gln Pro Arg Arg Pro His Pro
1               5                   10                  15

Arg Cys

<210> SEQ ID NO 78
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION

<400> SEQUENCE: 78

Gly Asn Asn Arg Pro Val Tyr Ile Pro Gln Pro Arg Pro Pro His Pro
1               5                   10                  15

Arg Cys

<210> SEQ ID NO 79
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION

<400> SEQUENCE: 79

Gly Asn Asn Arg Pro Val Tyr Ile Pro Arg Pro Arg Arg Pro His Pro
1               5                   10                  15

Arg Cys

<210> SEQ ID NO 80
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (18)..(18)
<223> OTHER INFORMATION: AMIDATION

<400> SEQUENCE: 80

Arg Trp Asn Arg Pro Val Tyr Ile Pro Arg Pro Arg Arg Pro His Pro
1               5                   10                  15

Arg Cys

<210> SEQ ID NO 81
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (18)..(18)
<223> OTHER INFORMATION: AMIDATION

<400> SEQUENCE: 81

Arg Trp Asn Arg Pro Val Tyr Ile Pro Arg Pro Arg Arg Pro His Pro
1               5                   10                  15

Arg Cys

<210> SEQ ID NO 82
<211> LENGTH: 18

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (17)..(17)
<223> OTHER INFORMATION: Orn
<220> FEATURE:
<221> NAME/KEY: MOD_RES
<222> LOCATION: (18)..(18)
<223> OTHER INFORMATION: AMIDATION

<400> SEQUENCE: 82

Arg Trp Asn Arg Pro Val Tyr Ile Pro Arg Pro Arg Arg Pro His Pro
1               5                   10                  15

Arg Cys

<210> SEQ ID NO 83
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (17)..(17)
<223> OTHER INFORMATION: Orn
<220> FEATURE:
<221> NAME/KEY: MOD_RES
<222> LOCATION: (18)..(18)
<223> OTHER INFORMATION: AMIDATION

<400> SEQUENCE: 83

Arg Trp Asn Arg Pro Val Tyr Ile Pro Arg Pro Arg Arg Pro His Pro
1               5                   10                  15

Arg Cys

<210> SEQ ID NO 84
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Alpha-N-Guanido-Ornithine

<400> SEQUENCE: 84

Xaa Asn Asn Arg Pro Val Tyr Ile Pro Arg Pro Arg Pro Pro His Pro
1               5                   10                  15

Arg Arg

<210> SEQ ID NO 85
<211> LENGTH: 18
<212> TYPE: PRT
<213> ORGANISM: Artificial Sequence
<220> FEATURE:
```

-continued

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Alpha-N-Guanido-Ornithine

<400> SEQUENCE: 85

Xaa Trp Asn Arg Pro Val Tyr Ile Pro Arg Pro Arg Pro Pro His Pro
1               5                   10                  15

Arg Leu

<210> SEQ ID NO 86
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Alpha-N-Guanido-Ornithine

<400> SEQUENCE: 86

Xaa Asn Asn Arg Pro Val Tyr Ile Pro Arg Pro Arg Arg Pro His Pro
1               5                   10                  15

Arg Leu

<210> SEQ ID NO 87
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Alpha-N-Guanido-Ornithine

<400> SEQUENCE: 87

Xaa Trp Asn Arg Pro Val Tyr Ile Pro Arg Pro Arg Arg Pro His Pro
1               5                   10                  15

Arg Leu

<210> SEQ ID NO 88
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Alpha-N-Guanido-Ornithine
<220> FEATURE:
<221> NAME/KEY: MOD_RES
<222> LOCATION: (18)..(18)
<223> OTHER INFORMATION: AMIDATION

<400> SEQUENCE: 88

Xaa Asn Asn Arg Pro Val Tyr Ile Pro Arg Pro Arg Arg Pro His Pro
1               5                   10                  15

Arg Leu
```

```
<210> SEQ ID NO 89
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Alpha-N-Guanido-Ornithine
<220> FEATURE:
<221> NAME/KEY: MOD_RES
<222> LOCATION: (18)..(18)
<223> OTHER INFORMATION: AMIDATION

<400> SEQUENCE: 89

Xaa Trp Asn Arg Pro Val Tyr Ile Pro Arg Pro Arg Arg Pro His Pro
1               5                   10                  15

Arg Leu

<210> SEQ ID NO 90
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION

<400> SEQUENCE: 90

Gly Asn Asn Arg Pro Val Tyr Ile Pro Gln Pro Arg Pro Pro His Pro
1               5                   10                  15

Arg Leu

<210> SEQ ID NO 91
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: AMIDATION

<400> SEQUENCE: 91

Gly Asn Asn Asp Pro Val Tyr Ile Pro Gln Pro Arg Pro Pro His Pro
1               5                   10                  15

Arg Leu

<210> SEQ ID NO 92
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Alpha-N-Guanido-Ornithine
<220> FEATURE:
<221> NAME/KEY: MOD_RES
<222> LOCATION: (18)..(18)
<223> OTHER INFORMATION: Leucine amide
```

<400> SEQUENCE: 92

Xaa Asn Asn Arg Pro Val Tyr Ile Pro Arg Pro Arg Pro Pro His Pro
1               5                   10                  15

Arg Xaa

<210> SEQ ID NO 93
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Alpha-N-Guanido-Ornithine

<400> SEQUENCE: 93

Xaa Asn Asn Arg Pro Val Tyr Ile Pro Arg Pro Arg Pro Pro His Pro
1               5                   10                  15

Arg Leu

<210> SEQ ID NO 94
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (3)..(4)
<223> OTHER INFORMATION: Any naturally occurring amino acid
<220> FEATURE:
<221> NAME/KEY: MOD_RES
<222> LOCATION: (10)..(11)
<223> OTHER INFORMATION: Any naturally occurring amino acid
<220> FEATURE:
<221> NAME/KEY: MOD_RES
<222> LOCATION: (17)..(18)
<223> OTHER INFORMATION: Any naturally occurring amino acid

<400> SEQUENCE: 94

Xaa Asn Xaa Xaa Pro Val Tyr Ile Pro Xaa Xaa Arg Pro Pro His Pro
1               5                   10                  15

Xaa Xaa

<210> SEQ ID NO 95
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MISC_FEATURE
<222> LOCATION: (2)..(2)
<223> OTHER INFORMATION: Xaa can be arginine or glutamine
<220> FEATURE:
<221> NAME/KEY: MOD_RES
<222> LOCATION: (3)..(4)

```
<223> OTHER INFORMATION: Any naturally occurring amino acid
<220> FEATURE:
<221> NAME/KEY: MOD_RES
<222> LOCATION: (10)..(11)
<223> OTHER INFORMATION: Any naturally occurring amino acid
<220> FEATURE:
<221> NAME/KEY: MOD_RES
<222> LOCATION: (17)..(17)
<223> OTHER INFORMATION: Any naturally occurring amino acid

<400> SEQUENCE: 95

Xaa Xaa Xaa Xaa Pro Val Tyr Ile Pro Xaa Xaa Arg Pro Pro His Pro
1               5                   10                  15

Xaa

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (3)..(4)
<223> OTHER INFORMATION: Any naturally occurring amino acid
<220> FEATURE:
<221> NAME/KEY: MOD_RES
<222> LOCATION: (10)..(11)
<223> OTHER INFORMATION: Any naturally occurring amino acid

<400> SEQUENCE: 96

Xaa Trp Xaa Xaa Pro Val Tyr Ile Pro Xaa Xaa Arg Pro Pro His Pro
1               5                   10                  15

<210> SEQ ID NO 97
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (3)..(4)
<223> OTHER INFORMATION: Any naturally occurring amino acid
<220> FEATURE:
<221> NAME/KEY: MOD_RES
<222> LOCATION: (10)..(11)
<223> OTHER INFORMATION: Any naturally occurring amino acid

<400> SEQUENCE: 97

Xaa Arg Xaa Xaa Pro Val Tyr Ile Pro Xaa Xaa Arg Pro Pro His Pro
1               5                   10                  15

<210> SEQ ID NO 98
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Any naturally occurring amino acid
<220> FEATURE:
<221> NAME/KEY: MISC_FEATURE
<222> LOCATION: (2)..(2)
<223> OTHER INFORMATION: Xaa can be arginine or glutamine
<220> FEATURE:
<221> NAME/KEY: MOD_RES
<222> LOCATION: (3)..(4)
<223> OTHER INFORMATION: Any naturally occurring amino acid
<220> FEATURE:
<221> NAME/KEY: MOD_RES
<222> LOCATION: (10)..(11)
<223> OTHER INFORMATION: Any naturally occurring amino acid

<400> SEQUENCE: 98

Xaa Xaa Xaa Xaa Cys Val Tyr Ile Pro Xaa Xaa Arg Pro Pro His Pro
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MISC_FEATURE
<222> LOCATION: (2)..(2)
<223> OTHER INFORMATION: Xaa can be arginine or glutamine
<220> FEATURE:
<221> NAME/KEY: MOD_RES
<222> LOCATION: (3)..(4)
<223> OTHER INFORMATION: Any naturally occurring amino acid
<220> FEATURE:
<221> NAME/KEY: MOD_RES
<222> LOCATION: (10)..(11)
<223> OTHER INFORMATION: Any naturally occurring amino acid

<400> SEQUENCE: 99

Xaa Xaa Xaa Xaa Arg Val Tyr Ile Pro Xaa Xaa Arg Pro Pro His Pro
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MISC_FEATURE
<222> LOCATION: (2)..(2)
<223> OTHER INFORMATION: Xaa can be arginine or glutamine
<220> FEATURE:
<221> NAME/KEY: MOD_RES
<222> LOCATION: (3)..(4)
<223> OTHER INFORMATION: Any naturally occurring amino acid
<220> FEATURE:
<221> NAME/KEY: MOD_RES
<222> LOCATION: (10)..(11)
<223> OTHER INFORMATION: Any naturally occurring amino acid

<400> SEQUENCE: 100

Xaa Xaa Xaa Xaa Pro Val Tyr Arg Pro Xaa Xaa Arg Pro Pro His Pro
1               5                   10                  15
```

```
<210> SEQ ID NO 101
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MISC_FEATURE
<222> LOCATION: (2)..(2)
<223> OTHER INFORMATION: Xaa can be arginine or glutamine
<220> FEATURE:
<221> NAME/KEY: MOD_RES
<222> LOCATION: (3)..(4)
<223> OTHER INFORMATION: Any naturally occurring amino acid
<220> FEATURE:
<221> NAME/KEY: MOD_RES
<222> LOCATION: (10)..(11)
<223> OTHER INFORMATION: Any naturally occurring amino acid

<400> SEQUENCE: 101

Xaa Xaa Xaa Xaa Pro Val Tyr Ile Pro Xaa Xaa Arg Arg Pro His Pro
1               5                   10                  15

<210> SEQ ID NO 102
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MISC_FEATURE
<222> LOCATION: (2)..(2)
<223> OTHER INFORMATION: Xaa can be arginine or glutamine
<220> FEATURE:
<221> NAME/KEY: MOD_RES
<222> LOCATION: (3)..(4)
<223> OTHER INFORMATION: Any naturally occurring amino acid
<220> FEATURE:
<221> NAME/KEY: MOD_RES
<222> LOCATION: (10)..(11)
<223> OTHER INFORMATION: Any naturally occurring amino acid

<400> SEQUENCE: 102

Xaa Xaa Xaa Xaa Pro Val Tyr Ile Pro Xaa Xaa Arg Pro Cys His Pro
1               5                   10                  15

<210> SEQ ID NO 103
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MISC_FEATURE
<222> LOCATION: (2)..(2)
<223> OTHER INFORMATION: Xaa can be arginine or glutamine
<220> FEATURE:
<221> NAME/KEY: MOD_RES
```

```
<222> LOCATION: (3)..(4)
<223> OTHER INFORMATION: Any naturally occurring amino acid
<220> FEATURE:
<221> NAME/KEY: MOD_RES
<222> LOCATION: (10)..(11)
<223> OTHER INFORMATION: Any naturally occurring amino acid

<400> SEQUENCE: 103

Xaa Xaa Xaa Xaa Pro Val Tyr Ile Pro Xaa Xaa Arg Pro Pro His Cys
1               5                   10                  15

<210> SEQ ID NO 104
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MISC_FEATURE
<222> LOCATION: (2)..(2)
<223> OTHER INFORMATION: Xaa can be arginine or glutamine
<220> FEATURE:
<221> NAME/KEY: MOD_RES
<222> LOCATION: (3)..(4)
<223> OTHER INFORMATION: Any naturally occurring amino acid
<220> FEATURE:
<221> NAME/KEY: MOD_RES
<222> LOCATION: (10)..(11)
<223> OTHER INFORMATION: Any naturally occurring amino acid
<220> FEATURE:
<221> NAME/KEY: MOD_RES
<222> LOCATION: (17)..(17)
<223> OTHER INFORMATION: Any naturally occurring amino acid

<400> SEQUENCE: 104

Xaa Xaa Xaa Xaa Pro Val Tyr Ile Pro Xaa Xaa Arg Pro Pro His Pro
1               5                   10                  15

Xaa Arg

<210> SEQ ID NO 105
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (3)..(4)
<223> OTHER INFORMATION: Any naturally occurring amino acid
<220> FEATURE:
<221> NAME/KEY: MOD_RES
<222> LOCATION: (11)..(11)
<223> OTHER INFORMATION: Any naturally occurring amino acid

<400> SEQUENCE: 105

Xaa Trp Xaa Xaa Pro Val Tyr Ile Pro Arg Xaa Arg Pro Pro His Pro
1               5                   10                  15

<210> SEQ ID NO 106
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (3)..(4)
<223> OTHER INFORMATION: Any naturally occurring amino acid
<220> FEATURE:
<221> NAME/KEY: MOD_RES
<222> LOCATION: (10)..(11)
<223> OTHER INFORMATION: Any naturally occurring amino acid

<400> SEQUENCE: 106

Xaa Trp Xaa Xaa Pro Val Tyr Ile Pro Xaa Xaa Arg Arg Pro His Pro
1               5                   10                  15

<210> SEQ ID NO 107
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MISC_FEATURE
<222> LOCATION: (2)..(2)
<223> OTHER INFORMATION: Xaa can be arginine or glutamine
<220> FEATURE:
<221> NAME/KEY: MOD_RES
<222> LOCATION: (3)..(4)
<223> OTHER INFORMATION: Any naturally occurring amino acid
<220> FEATURE:
<221> NAME/KEY: MOD_RES
<222> LOCATION: (11)..(11)
<223> OTHER INFORMATION: Any naturally occurring amino acid

<400> SEQUENCE: 107

Xaa Xaa Xaa Xaa Pro Val Tyr Ile Pro Arg Xaa Arg Arg Pro His Pro
1               5                   10                  15

<210> SEQ ID NO 108
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (3)..(4)
<223> OTHER INFORMATION: Any naturally occurring amino acid
<220> FEATURE:
<221> NAME/KEY: MOD_RES
<222> LOCATION: (11)..(11)
<223> OTHER INFORMATION: Any naturally occurring amino acid

<400> SEQUENCE: 108

Xaa Trp Xaa Xaa Pro Val Tyr Ile Pro Arg Xaa Arg Arg Pro His Pro
1               5                   10                  15

<210> SEQ ID NO 109
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (3)..(4)
<223> OTHER INFORMATION: Any naturally occurring amino acid
<220> FEATURE:
<221> NAME/KEY: MOD_RES
<222> LOCATION: (10)..(10)
<223> OTHER INFORMATION: Any naturally occurring amino acid

<400> SEQUENCE: 109

Xaa Trp Xaa Xaa Pro Val Tyr Ile Pro Xaa Arg Arg Pro Pro His Pro
1               5                   10                  15

<210> SEQ ID NO 110
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (3)..(4)
<223> OTHER INFORMATION: Any naturally occurring amino acid
<220> FEATURE:
<221> NAME/KEY: MOD_RES
<222> LOCATION: (10)..(10)
<223> OTHER INFORMATION: Any naturally occurring amino acid

<400> SEQUENCE: 110

Xaa Trp Xaa Xaa Pro Val Tyr Ile Pro Xaa Pro Arg Pro Pro His Pro
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MISC_FEATURE
<222> LOCATION: (2)..(2)
<223> OTHER INFORMATION: Xaa can be arginine or glutamine
<220> FEATURE:
<221> NAME/KEY: MOD_RES
<222> LOCATION: (3)..(4)
<223> OTHER INFORMATION: Any naturally occurring amino acid
<220> FEATURE:
<221> NAME/KEY: MOD_RES
<222> LOCATION: (10)..(10)
<223> OTHER INFORMATION: Any naturally occurring amino acid

<400> SEQUENCE: 111

Xaa Xaa Xaa Xaa Pro Val Tyr Ile Pro Xaa Arg Arg Pro Pro His Pro
1               5                   10                  15
```

```
<210> SEQ ID NO 112
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (3)..(4)
<223> OTHER INFORMATION: Any naturally occurring amino acid
<220> FEATURE:
<221> NAME/KEY: MOD_RES
<222> LOCATION: (10)..(10)
<223> OTHER INFORMATION: Any naturally occurring amino acid

<400> SEQUENCE: 112

Xaa Arg Xaa Xaa Pro Val Tyr Ile Pro Xaa Pro Arg Pro Pro His Pro
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MISC_FEATURE
<222> LOCATION: (2)..(2)
<223> OTHER INFORMATION: Xaa can be arginine or glutamine
<220> FEATURE:
<221> NAME/KEY: MOD_RES
<222> LOCATION: (3)..(4)
<223> OTHER INFORMATION: Any naturally occurring amino acid
<220> FEATURE:
<221> NAME/KEY: MOD_RES
<222> LOCATION: (10)..(10)
<223> OTHER INFORMATION: Any naturally occurring amino acid

<400> SEQUENCE: 113

Xaa Xaa Xaa Xaa Cys Val Tyr Ile Pro Xaa Pro Arg Pro Pro His Pro
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MISC_FEATURE
<222> LOCATION: (2)..(2)
<223> OTHER INFORMATION: Xaa can be arginine or glutamine
<220> FEATURE:
<221> NAME/KEY: MOD_RES
<222> LOCATION: (3)..(4)
<223> OTHER INFORMATION: Any naturally occurring amino acid
<220> FEATURE:
<221> NAME/KEY: MOD_RES
```

```
<222> LOCATION: (10)..(10)
<223> OTHER INFORMATION: Any naturally occurring amino acid

<400> SEQUENCE: 114

Xaa Xaa Xaa Xaa Arg Val Tyr Ile Pro Xaa Pro Arg Pro Pro His Pro
1               5                   10                  15

<210> SEQ ID NO 115
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MISC_FEATURE
<222> LOCATION: (2)..(2)
<223> OTHER INFORMATION: Xaa can be arginine or glutamine
<220> FEATURE:
<221> NAME/KEY: MOD_RES
<222> LOCATION: (3)..(4)
<223> OTHER INFORMATION: Any naturally occurring amino acid
<220> FEATURE:
<221> NAME/KEY: MOD_RES
<222> LOCATION: (10)..(10)
<223> OTHER INFORMATION: Any naturally occurring amino acid

<400> SEQUENCE: 115

Xaa Xaa Xaa Xaa Pro Val Tyr Arg Pro Xaa Pro Arg Pro Pro His Pro
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MISC_FEATURE
<222> LOCATION: (2)..(2)
<223> OTHER INFORMATION: Xaa can be arginine or glutamine
<220> FEATURE:
<221> NAME/KEY: MOD_RES
<222> LOCATION: (3)..(4)
<223> OTHER INFORMATION: Any naturally occurring amino acid
<220> FEATURE:
<221> NAME/KEY: MOD_RES
<222> LOCATION: (10)..(10)
<223> OTHER INFORMATION: Any naturally occurring amino acid

<400> SEQUENCE: 116

Xaa Xaa Xaa Xaa Pro Val Tyr Ile Pro Xaa Pro Arg Pro Cys His Pro
1               5                   10                  15

<210> SEQ ID NO 117
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Any naturally occurring amino acid
<220> FEATURE:
<221> NAME/KEY: MISC_FEATURE
<222> LOCATION: (2)..(2)
<223> OTHER INFORMATION: Xaa can be arginine or glutamine
<220> FEATURE:
<221> NAME/KEY: MOD_RES
<222> LOCATION: (3)..(4)
<223> OTHER INFORMATION: Any naturally occurring amino acid
<220> FEATURE:
<221> NAME/KEY: MOD_RES
<222> LOCATION: (10)..(10)
<223> OTHER INFORMATION: Any naturally occurring amino acid

<400> SEQUENCE: 117

Xaa Xaa Xaa Xaa Pro Val Tyr Ile Pro Xaa Pro Arg Pro Pro His Cys
1               5                   10                  15

<210> SEQ ID NO 118
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MISC_FEATURE
<222> LOCATION: (2)..(2)
<223> OTHER INFORMATION: Xaa can be arginine or glutamine
<220> FEATURE:
<221> NAME/KEY: MOD_RES
<222> LOCATION: (3)..(4)
<223> OTHER INFORMATION: Any naturally occurring amino acid
<220> FEATURE:
<221> NAME/KEY: MOD_RES
<222> LOCATION: (10)..(10)
<223> OTHER INFORMATION: Any naturally occurring amino acid

<400> SEQUENCE: 118

Xaa Xaa Xaa Xaa Pro Val Tyr Ile Pro Xaa Pro Arg Pro Pro His Pro
1               5                   10                  15

Arg Arg
```

MODIFIED APIDAECIN DERIVATIVES AS ANTIBIOTIC PEPTIDES

This application is a National Stage of PCT/EP2012/068620, filed Sep. 21, 2012, which claims benefit of German Patent Application No. 102011118026.9, filed Sep. 22, 2011, the disclosures of which are incorporated herein by reference in their entirety.

The Sequence Listing submitted Sep. 12, 2016 as a text file named "37578_0022U1_Revised_Sequence_Listing," created on Sep. 19, 2016, and having a size of 53,248 bytes is hereby incorporated by reference pursuant to 37 C.F.R. §1.52(e)(5).

INTRODUCTION

This invention relates to modified antibiotic peptides, particularly for use in medical applications. The invention further relates to compositions and methods for killing microorganisms such as bacteria, viruses or fungi, and to methods for treating microbial infections.

Despite notable advances in antibiotic therapy, the development of serious bacterial and fungal infections remains a growing problem. Each year, more than 40 million hospitalizations are required in the United States, during which more than 2 million patients come down with infections. 50-60% of these cases involve antibiotic-resistant bacteria. These diseases contracted during periods of hospitalization result in an estimated 60,000-70,000 deaths in the U.S. and up to 10,000 deaths in Germany.

Thus the need to develop new antibiotics is clear. One field of research in which current biochemistry, immunology and pharmaceuticals research efforts come together is inducible antibacterial peptides. Peptide antibiotics, ranging in size from 13 to more than one hundred amino acids, have been isolated from plants, animals and microbes (Boman, H. G. 1995).

A single animal has approximately 6-10 antimicrobial peptides, with each peptide often displaying an entirely different spectrum of activity (Barra, D. et al. 1998). It is known that the vast majority of antibacterial peptides, including the well-researched defensins, cecropins and magainins, act based on a "lytic/ionic" mechanism. A permeabilizing effect on the bacterial cytoplasmic membrane has been discussed as a common activity mechanism of these "lytic" peptides. This activity is based on a cationic, amphipathic structure, which forms hydrophilic ion (proton) channels in a lipid bilayer. The outflow of ions destroys the membrane potential required for many fundamental life processes, thereby killing off the cell. In higher concentrations, these lytic peptides often have a toxic effect on the cell membranes of mammals, which limits their suitability as potential pharmaceutical agents. Inserting proline into the α-helical antimicrobial peptide sequence decreases the ability of these peptides to permabilize the cytoplastic membrane of E. coli in proportion to the number of proline residues. It is therefore surprising that some of the most active native antibacterial peptides, at least with regard to some gram-negative pathogens, belong to the family of proline-rich peptides (Otvos, L. et al. 2000).

The secondary effects described above might be overcome by using antimicrobial peptides (AMP) that specifically detect a bacterial protein or some other intracellular or extracellular bacterial components, without cross-reactivity with mammalian analogues. This appears to be the case with proline-rich antimicrobial peptides, including apidaecins, drosocin and pyrrhocoricin, which were originally isolated from insects. Considering the enormous variations in size and biochemical properties of such peptides, it is no surprise that antibacterial peptide research has focused on structure action and configuration/action relationships. A full investigation of the natural antibacterial peptide repertoire of biological strength is not only important in terms of general biochemical issues, but is also of ongoing interest for the pharmaceuticals industry. Despite the problems of in vitro testing using peptide-based antibiotics, some natural, cationic antibacterial peptides have already reached the clinical trial phase (Boman, H. G. 1995). While some of these peptides have demonstrated activity as topical (local) agents in the early clinical trial phase, others have been active in systemic therapy. For example, the cationic protein rBPI 21, which is used for parental treatment of meningococcemia, has completed the third phase of clinical testing (Boman, H. G. 1995).

The members of the family of proline-rich peptides (e.g. apidaecin, drosocin and pyrrhocoricin) destroy bacteria not by permeabilizing the membrane thereof, but by binding stereospecifically to one or more target proteins. These potential interaction partners, of which the heat-shock protein DnaK has been studied extensively thus far (Boman, H. G. 1995), are inhibited by proline-rich peptides, presumably preventing proper protein folding and ultimately leading to cell death. Moreover, proline-rich peptides, in stark contrast to AMPs such as melittin or gramicidin which have a defined secondary structure, seem in vitro to have neither a hemolytic nor a toxic effect on eukaryotic cells. The development of new peptide-based antibiotics is influenced substantially by their stability in mammalian serum (25%), in addition to their antimicrobial activity. For example, drosocin is broken down within one hour, whereas pyrrhocoricin, with a half-life of 120 minutes, is far more stable in relation to proteases. In this process, not only are the N-terminus and C-terminus split off by amino- and carboxy peptidases, the peptides are also presumably broken down by endoproteases. The resulting metabolites are stable to some extent against further breakdown; however, most lose their antimicrobial activity (MIC values≥64 μg/mL).

Apidaecin is a peptide found in honeybee (*Apis mellfera*) hemolymph, where it plays an important role in fighting microbial infections. Studies have shown that apidaecin is active primarily against gram-negative bacteria (Li, W. F. 2006).

U.S. Pat. No. 5,300,629 A discloses apidaecins of the general formula:

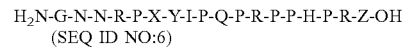
(SEQ ID NO:6)

in which X is valine or isoleucine and Z is leucine or isoleucine.

WO 9523513 A discloses apidaecin derivatives having sequence motifs

in which X1 is isoleucine or leucine, X2 is arginine or lysine, X3 is threonine, glutamine or arginine, X4 is tyrosine, glutamine or proline and X5 is valine or alanine.

Czihal et al. 2007 mentions that the apidaecin sequence has been modified with natural and modified amino acids so as to increase its antibacterial activity and its protease resistance. However, the abstract does not offer any details on the modifications, and particularly fails to mention any sequences or offer any suggestion as to which modifications have been successful.

WO 2009/013262 A1 discloses peptides of the general formula:

Sub₁-X₁ N X₂ X₃ P V Y I P X₄ X₅R P P H P-Sub₂
(SEQ ID NO:3)

in which Sub2 may contain Arg-Ile (RI).

Gobbo et al. 2006 discloses apidaecin peptoids in which the arginine residues (positions 4, 12 and 17) are replaced with corresponding N-substituted glycines. That is, the side chain in the apidaecin peptoids is shifted from the Cα to the Nα atom, resulting in a reduction in protease sensitivity. In Table 1 below, general formulas and individual sequences of previously known apidaecin derivatives and related peptides are compared in alignment:

TABLE 1

| Peptide/Document | Amino Acid Sequence* | SEQ ID No. |
|---|---|---|
| Native apidaecin 1a | GNNRPVYIPQPRPPHPRI | 1 |
| Native apidaecin 1b | GNNRPVYIPQPRPPHPRL | 2 |
| WO2009013262A1 | XNXXPVYIPXXRPPHP | 3 |
| WO9523513 A | XPXXXP | 4 |
|  | PRPPHPRX | 5 |
| U.S. Pat. No. 5,300,629 A | GNNRPXYIPQPRPPHPR | 6 |
| Drosocin | GKPRPYSPRPTSHPRPIRV | 7 |
| Fromaecin 1 | GRPNPVNNKPTPYPHL | 8 |

*X . . . varied positions

As is clear from Table 1, in the known apidaecin derivatives, particularly those positions that correspond to the amino acids Asn2, Pro5, Pro13, Pro14, His15 and Pro16 of native apidaecin are preserved (with the numbers of the positions of the amino acids corresponding to the original amino acid sequence of native apidaecin).

The activity of proline-rich antimicrobial peptides is highly complex since they must penetrate the cell membrane and infiltrate the cytoplasm in order to inhibit a specific intracellular bacterial target molecule without having a toxic effect on mammalian cells and blood cells. Another important feature is the stability of these peptides or peptide derivatives (including peptidomimetics) against breakdown by peptidases or proteases in blood and in the bacteria. Thus the ideal antibiotic peptide will have strong antibacterial activity (low MIC values), no cell toxicity, no hemolytic activity and a half-life of several hours in the blood.

The object of the invention is to develop new antibiotic peptides which particularly have an enhanced antibiotic effect and an expanded spectrum of activity against other strains of bacteria, particularly gram-positive bacteria such as Staphylococcus aureus.

DESCRIPTION

It has heretofore been assumed that apidaecin and derivatives thereof are ineffectual against gram-positive bacteria, and thus far, no apidaecin derivatives have been found that are scientifically effective against gram-positive bacteria, or the activity of such apidaecin derivatives has been found to be so low that they have not been considered medically useful. Unexpectedly, and in contrast to the prevailing opinion, the inventors have succeeded in identifying apidaecin derivatives which are also effective against gram-positive bacteria.

The invention thus relates to a peptide for use as a drug designed to fight infection caused by gram-positive bacteria and/or infection caused by both gram-positive and gram-negative bacteria. The present invention also relates to such a peptide or to a pharmaceutical composition containing such a peptide, a peptide multimer comprising at least two such peptides, a nucleic acid encoding for the peptide and a host cell containing the nucleic acid. The peptide described herein can also be used as an antibiotic against gram-negative bacteria. The peptide according to the invention will be described in the following.

According to the invention, the object is attained by the peptides according to FIG. 2, i.e., by those peptides of FIG. 1 that have a value of less than 1. A value of less than 1 indicates enhanced activity as compared with native apidaecin. The subject matter of this invention is therefore the peptides indicated in FIG. 2.

The object is further attained by a peptide containing an amino acid sequence according to general Formula A or B:

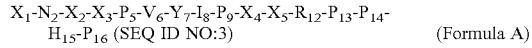

$X_1$-$N_2$-$X_2$-$X_3$-$P_5$-$V_6$-$Y_7$-$I_8$-$P_9$-$X_4$-$X_5$-$R_{12}$-$P_{13}$-$P_{14}$-$H_{15}$-$P_{16}$ (SEQ ID NO:3)    (Formula A)

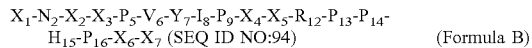

$X_1$-$N_2$-$X_2$-$X_3$-$P_5$-$V_6$-$Y_7$-$I_8$-$P_9$-$X_4$-$X_5$-$R_{12}$-$P_{13}$-$P_{14}$-$H_{15}$-$P_{16}$-$X_6$-$X_7$ (SEQ ID NO:94)    (Formula B)

The amino acid sequence according to Formula A or B preferably has at least 60%, more preferably at least 70%, and more preferably still at least 80% amino acid sequence identity to native apidaecin 1b according to SEQ ID No. 2. According to the invention, in Formula A or B:

$X_1$ is selected from the group of non-polar, aromatic, positively charged amino acid residues, amino acid residues containing a thiol group, amino acid residues containing a selenol group, proline and proline derivatives;

$N_2$, $X_2$ and $P_5$ are selected, independently of one another, from neutral and positively charged amino acid residues;

$X_3$ is selected from positively charged amino acid residues (preferably non-aromatic, particularly not histidine), amino acid residues containing a thiol group and amino acid residues containing a selenol group;

$V_6$ is selected from non-polar amino acid residues having at least 2 carbon atoms, preferably 2 to 8 carbon atoms, in the side chain, aromatic amino acid residues, positively charged amino acid residues, amino acid residues containing a thiol group, amino acid residues containing a selenol group, proline and proline derivatives;

$Y_7$ is selected from tyrosine, positively charged amino acid residues (preferably non-aromatic, particularly not histidine), amino acid residues containing a thiol group and amino acid residues containing a selenol group;

$I_8$ is selected from non-polar, aromatic amino acid residues having at least 2 and no more than 8 carbon atoms in the side chain, positively charged amino acid residues, amino acid residues containing a thiol group and amino acid residues containing a selenol group;

$P_9$, $P_{13}$, $P_{14}$ and $P_{16}$ are selected, independently of one another, from positively charged amino acid residues, amino acid residues containing a thiol group, amino acid residues containing a selenol group, non-polar aromatic amino acid residues, heteroaromatic amino acid residues, proline and proline derivatives;

$X_4$ is selected from neutral, positively charged amino acid residues, amino acid residues containing a thiol group and amino acid residues containing a selenol group;

$X_5$ is selected from proline, proline derivatives, positively charged amino acid residues, amino acid residues containing a thiol group and amino acid residues containing a selenol group;

$R_{12}$ is a positively charged amino acid residue (preferably non-aromatic, particularly not histidine);

$H_{15}$ is selected from histidine, positively charged amino acid residues, amino acid residues containing a thiol group and amino acid residues containing a selenol group;

$X_6$ is selected from positively charged amino acid residues, with $X_6$ preferably being (unaltered) arginine;

$X_7$ is selected from non-polar amino acid residues (preferably having at least 2 carbon atoms in the side chain, more preferably having 2-8 carbon atoms in the side chain), positively charged amino acid residues (preferably having at least 2 carbon atoms in the side chain, more preferably having 2-8 carbon atoms in the side chain), amino acid residues containing a thiol group and amino acid residues containing a selenol group.

In the peptide according to the invention, at least one of positions 2, 6, 8 to 11, 13 to 16 and 18 of SEQ ID No. 2 is modified in such a way that at least one of the following conditions applies to the peptide according to Formula A or B:

$N_2$ is selected from non-polar amino acid residues, preferably non-polar aromatic amino acid residues having 6 to 15, preferably 8 to 15, carbon atoms in the side chain, positively charged amino acid residues, amino acid residues containing a thiol group and amino acid residues containing a selenol group, with $N_2$ preferably being selected from arginine, ornithine, lysine, cysteine, selenocysteine, valine, isoleucine, methionine, phenylalanine and tryptophan, particularly preferably arginine, ornithine, lysine, cysteine, selenocysteine, phenylalanine and tryptophan, at least one of the residues selected from $P_5$, $V_6$, $Y_7$, $I_8$, $P_9$, $P_{13}$, $P_{14}$ and $P_{16}$, is a positively charged amino acid residue (preferably arginine, ornithine or lysine), an amino acid residue containing a thiol group or an amino acid residue containing a selenol group (preferably cysteine or selenocysteine), and/or $H_{15}$ is selected from amino acid residues containing a thiol group and amino acid residues containing a selenol group (preferably cysteine or selenocysteine) and/or $X_7$ is selected from positively charged amino acid residues, amino acid residues containing a thiol group and amino acid residues containing a selenol group, with $X_7$ preferably being selected from cysteine, lysine, arginine and ornithine.

In a preferred embodiment, the peptide is characterized in that at least one of positions 2, 5 to 11, 13 to 16 and 18 of SEQ ID No. 2 is modified such that at least one of the following conditions applies to the peptide according to Formula A or B:

$N_2$ is selected from non-polar amino acid residues, positively charged amino acid residues, amino acid residues containing a thiol group and amino acid residues containing a selenol group, with $N_2$ preferably being selected from tryptophan, arginine, lysine and cysteine, $X_4$ is selected from lysine, δ-hydroxylysine, ε-N-methyllysine, allo-hydroxylysine, cysteine and selenocysteine, at least one of the residues chosen from $P_5$, $V_6$, $Y_7$, $I_8$, $P_9$, $P_{11}$, $P_{13}$, $P_{14}$, $P_{16}$ and $X_7$ is a positively charged amino acid residue, an amino acid residue containing a thiol group or an amino acid residue containing a selenol group, and/or $H_{15}$ is selected from amino acid residues containing a thiol group and amino acid residues containing a selenol group, with $H_{15}$ preferably being cysteine.

In a further embodiment, the peptide is characterized in that at least one of the following positions of SEQ ID No. 2 is modified such that at least one of the following conditions applies to the 2 peptide according to Formula A or B:

$N_2$ is selected from non-polar amino acid residues, positively charged amino acid residues, amino acid residues containing a thiol group and amino acid residues containing a selenol group, with $N_2$ preferably being selected from tryptophan, arginine, lysine and cysteine, at least one of the residues chosen from $P_5$, $V_6$, $Y_7$, $I_8$, $P_9$, $P_{13}$, $P_{14}$, $P_{16}$ and $X_7$ is a positively charged amino acid residue, an amino acid residue containing a thiol group or an amino acid residue containing a selenol group, and/or $H_{15}$ is selected from amino acid residues containing a thiol group and amino acid residues containing a selenol group, with $H_{15}$ preferably being cysteine.

In a further embodiment, the peptide is characterized in that at least one of the following positions of SEQ ID No. 2 is modified such that at least one of the following conditions applies to the peptide according to Formula A or B:

$N_2$ is arginine or glutamine,

P5 is cysteine or arginine, at least one of the residues selected from $I_8$, $P_{13}$, $P_{14}$ and $X_7$ is arginine, and/or $P_{16}$ is cysteine, and optionally, $X_4$ is also arginine.

$X_7$ is preferably selected from positively charged amino acid residues, amino acid residues containing a thiol group and amino acid residues containing a selenol group, with $X_7$ particularly preferably being selected from cysteine, lysine, arginine and ornithine.

In one specific embodiment, 1, 2, 3, 4 or all 5 conditions are met. For example, the conditions for $N_2$ and $X_4$ may be met; or those for $N_2$ and at least one of the residues selected from $P_5$, $V_6$, $Y_7$, $I_8$, $P_9$, $P_{11}$, $P_{13}$, $P_{14}$, $P_{16}$ and $X_7$; or those for $N_2$ and His; or those for $N_2$, $X_4$ and at least one of the residues selected from $P_5$, $V_6$, $Y_7$, $I_8$, $P_9$, $P_{11}$, $P_{13}$, $P_{14}$, $P_{16}$ and $X_7$. The conditions for $X_4$ and at least one of the residues selected from $P_5$, $V_6$, $Y_7$, $I_8$, $P_9$, $P_{11}$, $P_{13}$, $P_{14}$, $P_{16}$ and $X_7$ and optionally $H_{15}$ may also be met. A person skilled in the art will know that the residues selected from $P_5$, $V_6$, $Y_7$, $I_8$, $P_9$, $P_{11}$, $P_{13}$, $P_{14}$, $P_{16}$ and $X_7$ can be selected independently of one another. He will also know that the above-stated condition may be met for 1, 2, 3, 4, 5, 6, 7, 8, 9 or all 10 residues.

Therefore, the peptide according to the invention contains no negatively charged amino acid residues.

If a positively charged amino acid residue is located at position $N_2$ in a peptide of Formula A or B according to the invention, it is preferably unsubstituted.

1. According to the invention, a preferred peptide is one which contains an amino acid sequence according to Formula A or B and in which $N_2$ and/or at least one of residues $P_5$, $V_6$, $Y_7$, $I_8$, $P_9$, $P_{11}$, $P_{13}$, $P_{14}$ and/or $P_{16}$ is as selected above, and in which the following applies: $H_{15}$ is selected from positively charged, non-aromatic amino acid residues, amino acid residues containing a thiol group and amino acid residues containing a selenol group, preferably from cysteine, lysine, arginine or ornithine.

2.

3. According to the invention, a further preferred peptide is one which contains an amino acid sequence according to Formula A or B and in which at least one of residues $P_5$, $V_6$, $Y_7$, $I_8$, $P_9$, $P_{11}$, $P_{13}$, $P_{14}$, and/or $P_{16}$ is as selected above, and in which the following applies: $N_2$ is selected from positively charged, non-aromatic amino acid residues, amino acid residues containing a thiol group and amino acid residues containing a selenol group, preferably from cysteine, lysine, arginine or ornithine.

The invention is based on a substitution analysis of apidaecin 1b:

GNNRPVYIPQPRPPHIPRL (SEQ ID No. 2).

Substitution analysis has shown that positions Asn2, Asn3 and Pro5 in the native peptide are particularly unfavorably filled, and that antibiotic activity can be optimized by substitution with any other amino acids that are not negatively charged. In the remaining positions of the native apidaecin 1b sequence, antibiotic activity can be improved particularly by substitution with positively charged amino acid residues (such as lysine or arginine) or with amino acid residues containing a thiol group (such as cysteine). Interestingly, the positioning of these amino acids within the sequence does not appear to play any particular role. It was important only for these amino acids to be present (see FIG. 1). Some of the peptides that exhibit enhanced antimicrobial activity, identified through substitution analysis, were studied further with respect to their antibacterial activity against various strains of bacteria, particularly gram-positive bacteria. In these studies it was found that the peptides according to the invention also exhibit advantageous antibacterial activity against gram-positive bacteria such as *S. aureus*.

Preferred peptides according to the invention contain at least one additional amino acid residue X6 and optionally one additional amino acid residue X7 at the C-terminus, wherein X6 is selected from positively charged amino acid residues, and wherein X7 is selected from positively charged amino acid residues, amino acid residues containing a thiol group and amino acid residues containing a selenol group. One preferred peptide of this type comprises at least one amino acid sequence according to general Formula B or C:

$$X_1-N_2-X_2-X_3-P_5-V_6-Y_7-I_8-P_9-X_4-X_5-R_{12}-P_{13}-P_{14}-H_{15}-P_{16}-X_6 \text{ (SEQ ID NO:95)} \quad \text{(Formula C)}$$

Peptides of Formula C according to the invention, as compared with those of Formula A, further contain the additional amino acid residue $X_6$, as defined above. $X_6$ is preferably arginine.

Preferred peptides according to the invention are apidaecin derivatives that have at least one of the following mutations in the amino acid sequence of apidaecin 1b (SEQ ID No. 2), wherein the numbers refer to the positions within the amino acid sequence according to SEQ ID No. 2:

Asn2→Trp, Arg, Lys oder Cys, (Position $X_1$ in Formula A, B and C)
Asn3→Trp, Arg, Lys oder Cys, (Position $N_2$ in Formula A, B and C)
Pro5→Cys, Lys oder Arg, (Position $P_5$ in Formula A, B and C)
Ile8→Arg, Lys oder Cys, (Position $I_8$ in Formula A, B and C)
Pro13→Arg, Lys oder Cys, (Position $P_{13}$ in Formula A, B and C)
Pro14→Cys, Lys oder Arg, (Position $P_{14}$ in Formula A, B and C)
Pro16→Arg, Cys oder Lys, (Position $P_{16}$ in Formula A, B and C)
Leu18→Arg, Lys oder Cys (Position $X_7$ in Formula B)

The remaining positions are unchanged or are preferably selected as described below and above.

The peptides according to the invention preferably have at least 16 amino acid residues, more preferably at least 18, and preferably up 50 amino acid residues.

The peptide according to the invention contains no negatively charged amino acid residues. A negatively charged amino acid residue within the context of the invention contains an amino acid side chain that is negatively charged under physiological conditions. Physiological conditions within the context of the invention are a pH value of 7.4, a temperature of 37° C. and an osmotic pressure of 300 mOsmol/kg. A positively charged amino acid residue within the context of the invention contains an amino acid side chain that is positively charged under physiological conditions. Positively charged residues are preferably non-aromatic and are preferably selected from arginine, lysine, δ-hydroxylysine, homoarginine, 2,4-diaminobutyric acid, β-homoarginine, D-arginine, arginal (—COOH in arginine is replaced by —CHO), 2-amino-3-guanidinopropionic acid, 2-amino-4-guanidinobutyric acid, nitroarginine (preferably N(G)-nitroarginine), nitrosoarginine (preferably N(G)-nitrosoarginine), methylarginine (preferably N-methylarginine), ε-N-methyllysine, allo-hydroxylysine, 2,3-diaminopropionic acid, 2,2'-diaminopimelic acid, ornithine, sym-dimethylarginine, asym-dimethylarginine, 2,6-diaminohexanoic acid, p-aminobenzoic acid and 3-aminotyrosine, and less preferably are aromatic residues such as histidine, 1-methylhistidine and 3-methylhistidine.

A neutral amino acid residue contains an amino acid side chain that is uncharged under physiological conditions. Neutral amino acid residues are therefore neither positively nor negatively charged under physiological conditions. The term neutral amino acid residue encompasses polar and non-polar amino acid residues.

A polar amino acid residue has at least one polar group in the amino acid side chain. These polar groups are uncharged under physiological conditions, and are selected from hydroxyl-, sulfhydryl-, amine-, amide- and ester groups, and from other groups that allow the formation of hydrogen bridges. Preferred neutral polar amino acid residues are selected from asparagine, cysteine, glutamine, serine, threonine, tyrosine, citrulline, N-methylserine, homoserine, allo-threonine, 3,5-dinitrotyrosine and β-homoserine.

A non-polar (or hydrophobic) amino acid residue has no polar groups and contains an amino acid side chain that is uncharged under physiological conditions, preferably with a hydropathy index greater than 0, particularly preferably greater than 3. Preferred non-polar, hydrophobic side chains are selected from H, alkyl-, alkylene-, alkoxy-, alkenoxy-, alkylsulfanyl- and alkenylsulfanyl residues having 1 to 10, preferably 2 to 6 carbon atoms, and aryl residues having 5 to 12 carbon atoms. Preferred amino acid residues having a non-polar, hydrophobic side chain are selected from glycine, alanine, leucine, isoleucine, valine, methionine, alanine, phenylalanine, tryptophan, N-methylleucine, tert-butyl glycine, cyclohexylalanine, β-alanine, 1-amino-cylcohexyl carboxylic acid, N-methylisoleucine, norleucine, norvaline and N-methylvaline.

Aromatic amino acid residues have at least one aryl or heteroaryl ring. The term encompasses polar and non-polar aromatic amino acid residues, with polar and non-polar being as defined above. Preferred polar aromatic amino acid residues are selected from aryl residues having 5 to 12 carbon atoms and carrying at least one polar group, and from heteroaromatic amino acid residues. Preferred heteroaromatic amino acid residues are heteroaryl residues having 3 to 10 carbon atoms and 1 to 4 heteroatoms (preferably N, S or O) in the ring system, particularly preferably histidine. Particularly preferred polar aromatic amino acid residues are selected from tyrosine, 3,5-dinitrotyrosine, histidine and histidine derivatives. The term histidine derivative refers to an amino acid residue derived from histidine, preferably obtained from histidine by the structural modification of preferably precisely one or two functional groups. Preferred histidine derivatives are C1-C3-alkylated (preferably N-alkyl) histidines, particularly N-methyl histidine. Preferred non-polar aromatic amino acid residues are selected from aryl residues having 5 to 12 carbon atoms and carrying no polar groups. Particularly preferred non-polar aromatic amino acid residues are tryptophan, phenylalanine, phenylglycine, homophenylalanine, 4-tert-butylphenylalanine, methyltryptophan, naphtylalanine, diphenylalanine, methylphenylalanine, phenyl-phenylalanine and benzoylphenylalanine.

Amino acid residues containing a thiol group or selenol group are preferably selected from alkyl-alkoxy-, alkenoxy-, alkylsulfanyl- and alkenylsulfanyl residues having 1 to 10, preferably 2 to 6 carbon atoms, or aryl residues having 5 to 12 carbon atoms, and carrying at least one free (unsubstituted) thiol group (—SH) or selenol group (—SeH). Particularly preferred amino acid residues containing a thiol group or selenol group are cysteine and selenocysteine.

The term proline derivative refers to an amino acid residue derived from proline, preferably obtained from proline by the structural modification of preferably precisely one or two functional groups. Preferred proline derivatives are selected from β-cyclohexylalanine, 3,4-cis-methanoproline, 3,4-dehydroproline, hydroxyproline, mercaptoproline, thioproline, fluoroproline and homoproline. The term hydroxyproline includes cis-4-hydroxyproline, trans-4-hydroxyproline, cis-3-hydroxyproline and trans-3-hydroxyproline, for example. Therefore, the term hydroxyproline derivative refers to an amino acid residue derived from hydroxyproline, preferably obtained from hydroxyproline by the structural modification of a functional group. Preferred hydroxyproline derivatives are selected from hydroxy-β-cyclohexylalanine and the above-stated proline derivatives that are substituted with a hydroxyl group.

In preferred peptides of Formulas A, B and C according to the invention, the amino acid residue $X_1$ is preferably selected from arginine, lysine, δ-hydroxylysine, homoarginine, 2,4-diaminobutyric acid, β-homoarginine, D-arginine, arginal, 2-amino-3-guanidinopropionic acid, nitroarginine, N-methylarginine, ε-N-methyllysine, allo-hydroxylysine, 2,3-diaminopropionic acid, 2,2'-diaminopimelic acid, ornithine, sym-dimethylarginine, asym-dimethylarginine, 2,6-diaminohexanoic acid, p-aminobenzoic acid, 3-aminotyrosine, glycine, alanine, valine, isoleucine, leucine, methionine, N-methylleucine, tert.-butyl glycine, cyclohexylalanine, β-alanine, I-amino-cylcohexyl carboxylic acid, N-methylisoleucine, norleucine, norvaline, N-methylvaline, cysteine, selenocysteine, phenylalanine, tryptophan, phenylglycine, homophenylalanine, 4-tert-butylphenylalanine, methyltryptophan, naphtylalanine, diphenylalanine, methylphenylalanine, phenyl-phenylalanine, benzoylphenylalanine, histidine, N-methylhistidine, 3,5-dinitrotyrosine, tyrosine, proline, β-cyclohexylalanine, 3,4-cis-methanoproline, 3,4-dehydroproline, homoproline, mercaptoproline, thioproline, fluoroproline and hydroxyproline. $X_1$ is preferably selected from non-polar amino acid residues, preferably alanine, glycine, phenylalanine, methionine, isoleucine, valine, Leucine and proline, particularly leucine and proline, and aromatic amino acid residues such as tryptophan and tyrosine, and less preferably histidine, and particularly preferably positively charged residues, particularly lysine, arginine and cysteine. $X_1$ is particularly preferably selected from cysteine, lysine, arginine and ornithine or unmodified glycine.

In preferred peptides of Formulas A, B and C according to the invention, amino acid residues $N_2$, $X_2$ and $P_5$ are selected from all non-negatively charged amino acids. Glycine is less preferable for $X_2$, and alanine is less preferable for $P_5$. Amino acid residues $N_2$, $X_2$ and $P_5$ are preferably selected, independently of one another, from arginine, lysine, δ-hydroxylysine, homoarginine, β-homoarginine, D-arginine, arginal, 2,4-diaminobutyric acid, 2-amino-3-guanidinopropionic acid, nitroarginine, nitrosoarginine, N-methylarginine, ε-N-methyllysine, allo-hydroxylysine, 2,3-diaminopropionic acid, 2,2'-diaminopimelic acid, ornithine, sym-dimethylarginine, asym-dimethylarginine, 2,6-diaminohexanoic acid, p-aminobenzoic acid, 3-aminotyrosine, asparagine, cysteine, selenocysteine, glutamine, serine, threonine, citrulline, N-methylserine, homoserine, allo-threonine, tyrosine, 3,5-dinitrotyrosine, histidine, N-methylhistidine, phenylalanine, tryptophan, phenylglycine, homophenylalanine, 4-tert-butylphenylalanine, methyltryptophan, naphtylalanine, diphenylalanine, methylphenylalanine, phenyl-phenylalanine, benzoylphenylalanine, β-homoserine, proline, β-cyclohexylalanine, 3,4-cis-methanoproline, 3,4-dehydroproline, homoproline, mercaptoproline, thioproline, fluoroproline and hydroxyproline. $N_2$ is particularly preferably selected from cysteine, tryptophan, phenylalanine, lysine, arginine and ornithine, or unmodified asparagine. $X_2$ is particularly preferably selected from cysteine, lysine, arginine, ornithine and homoarginine, or unmodified asparagine. $P_5$ is particularly preferably selected from cysteine, lysine, arginine, ornithine, histidine and tryptophan, or unmodified proline.

In preferred peptides of Formulas A, B and C according to the invention, amino acid residue $X_3$ is selected from arginine, lysine, δ-hydroxylysine, homoarginine, β-homoarginine, D-arginine, arginal, 2,4-diaminobutyric acid, β-homoarginine, 2-amino-3-guanidinopropionic acid, nitroarginine, nitrosoarginine, N-methylarginine, ε-N-methyllysine, allo-hydroxylysine, 2,3-diaminopropionic acid, 2,2'-diaminopimelic acid, ornithine, sym-dimethylarginine, asym-dimethylarginine, 2,6-diaminohexanoic acid, p-aminobenzoic acid, cysteine and selenocysteine. $X_3$ is particularly preferably selected from arginine, lysine and cysteine, particularly arginine.

In preferred peptides of Formulas A, B and C according to the invention, amino acid $V_4$ is selected from arginine, lysine, δ-hydroxylysine, homoarginine, β-homoarginine, D-arginine, arginal, 2,4-diaminobutyric acid, β-homoarginine, 2-amino-3-guanidinopropionic acid, nitroarginine, nitrosoarginine, N-methylarginine, ε-N-methyllysine, allo-hydroxylysine, 2,3-diaminopropionic acid, 2,2'-diaminopimelic acid, ornithine, sym-dimethylarginine, asym-dimethylarginine, 2,6-diaminohexanoic acid, p-aminobenzoic acid, valine, isoleucine, leucine, methionine, N-methylleucine, tert.-butyl glycine, cyclohexylalanine, I-amino-cylcohexyl carboxylic acid, N-methylisoleucine, norleucine, norvaline, N-methylvaline, phenylalanine, phenylglycine, homophenylalanine, 4-tert-butylphenylalanine, methyltryptophan, naphtylalanine, diphenylalanine, methylphenylalanine, phenyl-phenylalanine, benzoylphenylalanine, histidine, N-methylhistidine, tryptophan, tyrosine, cysteine, selenocysteine, proline, β-cyclohexylalanine, 3,4-cis-methanoproline, 3,4-dehydroproline, homoproline, mercaptoproline, thioproline, fluoroproline and hydroxyproline. $V_6$ is preferably selected from positively charged amino acid residues, preferably arginine, lysine and cysteine, and less preferably from aromatic residues such as histidine, N-methylhistidine, tryptophan, 3,5-dinitrotyrosine and tyrosine, and non-polar residues (having more than two carbon atoms), such as isoleucine and proline. $V_6$ is particularly preferably selected from arginine, lysine, cysteine and tryptophan, or unmodified valine.

In preferred peptides of Formulas A, B and C according to the invention, amino acid $Y_7$ is selected from tyrosine, arginine, lysine, δ-hydroxylysine, homoarginine, β-homoarginine, D-arginine, arginal, 2,4-diaminobutyric acid, β-homoarginine, 2-amino-3-guanidinopropionic acid, nitroarginine, nitrosoarginine, N-methylarginine, ε-N-methyllysine, allo-hydroxylysine, 2,3-diaminopropionic acid, 2,2'-diaminopimelic acid, ornithine, sym-dimethylarginine, asym-dimethylarginine, 2,6-diaminohexanoic acid, p-aminobenzoic acid, cysteine and selenocysteine. $Y_7$ is preferably selected from positively charged amino acid residues, such as arginine and lysine, and cysteine. $Y_7$ is particularly preferably selected from arginine, ornithine, lysine and cysteine, or unmodified tyrosine.

In preferred peptides of Formulas A, B and C according to the invention, amino acid residue. $I_8$ is selected from arginine, lysine, δ-hydroxylysine, homoarginine, β-homoarginine, D-arginine, arginal, 2,4-diaminobutyric acid, 2-amino-3-guanidinopropionic acid, nitroarginine, nitrosoarginine, N-methylarginine, ε-N-methyllysine, allo-hydroxylysine, 2,3-diaminopropionic acid, 2,2'-diaminopimelic acid, ornithine, sym-dimethylarginine, asym-dimethylarginine, 2,6-diaminohexanoic acid, p-aminobenzoic acid, 3-aminotyrosine, cysteine, selenocysteine, valine, isoleucine, leucine, N-methylleucine, tert.-butyl glycine, cyclohexylalanine, I-amino-cylcohexyl carboxylic acid, N-methylisoleucine, norleucine, norvaline, N-methylvaline, phenylalanine, phenylglycine, homophenylalanine, 4-tert-butylphenylalanine, methyltryptophan, naphtylalanine, diphenylalanine, methylphenylalanine, phenyl-phenylalanine, benzoylphenylalanine, histidine, N-methylhistidine and tyrosine. $I_8$ is preferably selected from positively charged amino acid residues, such as arginine and lysine, and cysteine, and somewhat less preferably from aromatic residues (having a maximum of 8 carbon atoms) such as histidine, phenylalanine and tyrosine. $I_8$ is particularly preferably selected from arginine, ornithine, lysine, histidine and cysteine, or unmodified isoleucine.

In preferred peptides of Formulas A, B and C according to the invention, amino acid residues $P_9$, $P_{13}$, $P_{14}$ and $P_{16}$ are selected, independently of one another, from arginine, lysine, δ-hydroxylysine, homoarginine, β-homoarginine, D-arginine, arginal, 2,4-diaminobutyric acid, 2-amino-3-guanidinopropionic acid, nitroarginine, nitrosoarginine, N-methylarginine, ε-N-methyllysine, allo-hydroxylysine, 2,3-diaminopropionic acid, 2,2'-diaminopimelic acid, ornithine, sym-dimethylarginine, asym-dimethylarginine, 2,6-diaminohexanoic acid, p-aminobenzoic acid, 3-aminotyrosine, cysteine, selenocysteine, phenylalanine, tryptophan, phenylglycine, homophenylalanine, 4-tert-butylphenylalanine, methyltryptophan, naphtylalanine, diphenylalanine, methylphenylalanine, phenyl-phenylalanine, benzoylphenylalanine, histidine, N-methylhistidine, proline, β-cyclohexylalanine, 3,4-cis-methanoproline, 3,4-dehydroproline, homoproline, mercaptoproline, thioproline, fluoroproline and hydroxyproline. Amino acid residues $P_9$, $P_{13}$, $P_{14}$ and $P_{16}$ are preferably selected, independently of one another, from positively charged amino acid residues such as arginine and lysine, and cysteine, and, in the case of $P_9$, less preferably from heteroaromatic residues, such as histidine, and non-polar aromatic amino acid residues, phenylalanine and tryptophan. Particularly preferably, amino acid residues $P_9$, $P_{13}$, $P_{14}$ and $P_{16}$ are selected, independently of one another, from arginine, ornithine, lysine and cysteine, or unmodified proline.

In preferred peptides of Formulas A, B and C according to the invention, amino acid residue $X_4$ is selected from arginine, lysine, δ-hydroxylysine, homoarginine, β-homoarginine, D-arginine, arginal, 2,4-diaminobutyric acid, 2-amino-3-guanidinopropionic acid, nitroarginine, nitrosoarginine, N-methylarginine, ε-N-methyllysine, allo-hydroxylysine, 2,3-diaminopropionic acid, 2,2'-diaminopimelic acid, ornithine, sym-dimethylarginine, asym-dimethylarginine, 2,6-diaminohexanoic acid, p-aminobenzoic acid, 3-aminotyrosine, cysteine, selenocysteine, glutamine, citrulline, isoleucine, leucine, N-methylleucine, tert.-butyl glycine, cyclohexylalanine, 1-amino-cylcohexyl carboxylic acid, N-methylisoleucine, norleucine, norvaline, N-methylvaline, phenylalanine, tryptophan, phenylglycine, homophenylalanine, 4-tert-butylphenylalanine, methyltryptophan, naphtylalanine, diphenylalanine, methylphenylalanine, phenyl-phenylalanine, benzoylphenylalanine, histidine, N-methylhistidine, 3,5-dinitrotyrosine and tyrosine. $X_4$ is preferably selected from positively charged amino acid residues, such as arginine and lysine, and cysteine, and somewhat less preferably isoleucine, leucine, histidine and phenylalanine. $X_4$ is particularly preferably selected from arginine, ornithine, lysine, histidine and cysteine, or unmodified glutamine.

In preferred peptides of Formulas A, B and C according to the invention, amino acid residue $X_5$ is selected from arginine, lysine, δ-hydroxylysine, homoarginine, β-homoarginine, D-arginine, arginal, 2,4-diaminobutyric acid, 2-amino-3-guanidinopropionic acid, nitroarginine, nitrosoarginine, N-methylarginine, ε-N-methyllysine, allo-hydroxylysine, 2,3-diaminopropionic acid, 2,2'-diaminopimelic acid, ornithine, sym-dimethylarginine, asym-dimethylarginine, 2,6-diaminohexanoic acid, p-aminobenzoic acid, 3-aminotyrosine, cysteine, proline, β-cyclohexylalanine, 3,4-cis-methanoproline, 3,4-dehydroproline, homoproline, mercaptoproline, thioproline, fluoroproline and hydroxyproline. $X_5$ is preferably selected from positively charged amino acid residues, such as arginine and lysine, and cysteine, and somewhat less preferably from non-polar aromatic amino acid residues such as phenylalanine and tryptophan. $X_5$ is particularly preferably selected from arginine, ornithine, lysine, histidine and cysteine, or unmodified glutamine.

In preferred peptides of Formulas A, B and C according to the invention, amino acid residue $R_{12}$ is selected from arginine, lysine, δ-hydroxylysine, homoarginine, β-homoarginine, D-arginine, arginal, 2,4-diaminobutyric acid, 2-amino-3-guanidinopropionic acid, nitroarginine, nitrosoarginine, N-methylarginine, ε-N-methyllysine, allo-hydroxylysine, 2,3-diaminopropionic acid, 2,2'-diaminopimelic acid, ornithine, sym-dimethylarginine, asym-dimethylarginine, 2,6-diaminohexanoic acid, p-aminobenzoic acid and 3-aminotyrosine. $R_{12}$ is particularly preferably arginine, homoarginine, ornithine or lysine.

In preferred peptides of Formulas A, B and C according to the invention, the amino acid residue $H_{15}$ is selected from histidine, N-methylhistidine, arginine, lysine, δ-hydroxylysine, homoarginine, β-homoarginine, D-arginine, arginal, 2,4-diaminobutyric acid, 2-amino-3-guanidinopropionic acid, nitroarginine, nitrosoarginine, N-methylarginine, ε-N- methyllysine, allo-hydroxylysine, 2,3-diaminopropionic acid, 2,2'-diaminopimelic acid, ornithine, sym-dimethylarginine, asym-dimethylarginine, 2,6-diaminohexanoic acid, p-aminobenzoic acid and 3-aminotyrosine and cysteine. $H_{15}$ is particularly preferably arginine, homoarginine, ornithine, lysine, cysteine or unmodified histidine.

In preferred peptides according to the invention, 1 to 10, particularly preferably no more than 7, most preferably no more than 5 amino acid residues are modified as described above in relation to the native amino acid sequence of apidaecin 1b (SEQ ID No. 2). The remaining amino acid residues correspond to the respective amino acid at the corresponding position in native apidaecin 1b (SEQ ID No. 2). The peptide according to the invention preferably contains at least 3, and more preferably at least 4 positively charged amino acid residues, and particularly preferably 5 to 10 positively charged amino acid residues. The peptide preferably contains at least 4, more preferably at least 5, and preferably no more than 8 proline residues. The peptide further preferably contains at least one cysteine residue, and preferably no more than three cysteine residues.

Preferred peptides according to the invention contain at least one amino acid sequence according to any of general Formulas 1 to 10, in which residues $X_1$ to $X_4$ and $N_2$ have the meanings stated above for Formulas A, B and C, and the remaining amino acid residues correspond to the IUPAC one-letter code:

$X_1$-W-$X_2$-$X_3$-$P_5$-$V_6$-$Y_7$-$I_8$-$P_9$-$X_4$-$X_5$-$R_{12}$-$P_{13}$-$P_{14}$-$H_{15}$-$P_{16}$ (SEQ ID NO:96)

$X_1$-R-$X_2$-$X_3$-$P_5$-$V_6$-$Y_7$-$I_8$-$P_9$-$X_4$-$X_5$-$R_{12}$-$P_{13}$-$P_{14}$-$H_{15}$-$P_{16}$ (SEQ ID NO:97)

$X_1$-$N_2$-$X_2$-$X_3$-C-$V_6$-$Y_7$-$I_8$-$P_9$-$X_4$-$X_5$-$R_{12}$-$P_{13}$-$P_{14}$-$H_{15}$-$P_{16}$ (SEQ ID NO:98)

$X_1$-$N_2$-$X_2$-$X_3$-R-$V_6$-$Y_7$-$I_8$-$P_9$-$X_4$-$X_5$-$R_{12}$-$P_{13}$-$P_{14}$-$H_{15}$-$P_{16}$ (SEQ ID NO:99)

$X_1$-$N_2$-$X_2$-$X_3$-$P_5$-$V_6$-$Y_7$-R-$P_9$-$X_4$-$X_5$-$R_{12}$-$P_{13}$-$P_{14}$-$H_{15}$-$P_{16}$ (SEQ ID NO:100)

$X_1$-$N_2$-$X_2$-$X_3$-$P_5$-$V_6$-$Y_7$-$I_8$-$P_9$-$X_4$-$X_5$-$R_{12}$-R-$P_{14}$-$H_{15}$-$P_{16}$ (SEQ ID NO:101)

$X_1$-$N_2$-$X_2$-$X_3$-$P_5$-$V_6$-$Y_7$-$I_8$-$P_9$-$X_4$-$X_5$-$R_{12}$-$P_{13}$-C-$H_{15}$-$P_{16}$ (SEQ ID NO:102)

$X_1$-$N_2$-$X_2$-$X_3$-$P_5$-$V_6$-$Y_7$-$I_8$-$P_9$-$X_4$-$X_5$-$R_{12}$-$P_{13}$-$P_{14}$-$H_{15}$-C (SEQ ID NO:103)

$X_1$-$N_2$-$X_2$-$X_3$-$P_5$-$V_6$-$Y_7$-$I_8$-$P_9$-$X_4$-$X_5$-$R_{12}$-$P_{13}$-$P_{14}$-$H_{15}$-$P_{16}$-$X_6$-$R_{18}$ (SEQ ID NO:104)

$X_1$-W-$X_2$-$X_3$-$P_5$-$V_6$-$Y_7$-$I_8$-$P_9$-R-$X_5$-$R_{12}$-$P_{13}$-$P_{14}$-$H_{15}$-$P_{16}$ (SEQ ID NO:105)

$X_1$-W-$X_2$-$X_3$-$P_5$-$V_6$-$Y_7$-$I_8$-$P_9$-$X_4$-$X_5$-$R_{12}$-R-$P_{14}$-$H_{15}$-$P_{16}$ (SEQ ID NO:106)

$X_1$-$N_2$-$X_2$-$X_3$-$P_5$-$V_6$-$Y_7$-$I_8$-$P_9$-R-$X_5$-$R_{12}$-R-$P_{14}$-$H_{15}$-$P_{16}$ (SEQ ID NO:107)

$X_1$-W-$X_2$-$X_3$-$P_5$-$V_6$-$Y_7$-$I_8$-$P_9$-R-$X_5$-$R_{12}$-R-$P_{14}$-$H_{15}$-$P_{16}$ (SEQ ID NO:108)

and:

$X_1$-W-$X_2$-$X_3$-P-V-Y-I-P-$X_4$-R-R-P-P-H-P (SEQ ID NO:109)     (Formula 1)

$X_1$-W-$X_2$-$X_3$-P-V-Y-I-P-$X_4$-P-R-P-P-H-P (SEQ ID NO:110)     (Formula 2)

$X_1$-$N_2$-$X_2$-$X_3$-P-V-Y-I-P-$X_4$-R-R-P-P-H-P (SEQ ID NO:111)     (Formula 3)

$X_1$-R-$X_2$-$X_3$-P-V-Y-I-P-$X_4$-P-R-P-P-H-P (SEQ ID NO:112)     (Formula 4)

$X_1$-$N_2$-$X_2$-$X_3$-C-V-Y-I-P-$X_4$-P-R-P-P-H-P (SEQ ID NO:113)     (Formula 5)

$X_1$-$N_2$-$X_2$-$X_3$-R-V-Y-I-P-$X_4$-P-R-P-P-H-P (SEQ ID NO:114)     (Formula 6)

$X_1$-$N_2$-$X_2$-$X_3$-P-V-Y-R-P-$X_4$-P-R-P-P-H-P (SEQ ID NO:115)     (Formula 7)

$X_1$-$N_2$-$X_2$-$X_3$-P-V-Y-I-P-$X_4$-P-R-P-C-H-P (SEQ ID NO:116)     (Formula 8)

$X_1$-$N_2$-$X_2$-$X_3$-P-V-Y-I-P-$X_4$-P-R-P-P-H-C (SEQ ID NO:117)     (Formula 9)

$X_1$-$N_2$-$X_2$-$X_3$-P-V-Y-I-P-$X_4$-P-R-P-P-H-P-R-R (SEQ ID NO:118)     (Formula 10)

Particularly preferred is a peptide of general Formula A', B' or C' according to the invention, in which the meanings of the individual amino acid residues are as described above:

NT-$X_1$-$N_2$-$X_2$-$X_3$-$P_5$-$V_6$-$Y_7$-$I_8$-$P_9$-$X_4$-$X_5$-$R_{12}$-$P_{13}$-$P_{14}$-$H_{15}$-$P_{16}$-CT (SEQ ID NO:3)     (Formula A')

NT-$X_1$-$N_2$-$X_2$-$X_3$-$P_5$-$V_6$-$Y_7$-$I_8$-$P_9$-$X_4$-$X_5$-$R_{12}$-$P_{13}$-$P_{14}$-$H_{15}$-$P_{16}$-$X_6$-CT (SEQ ID NO:95)     (Formula C')

NT-$X_1$-$N_2$-$X_2$-$X_3$-$P_5$-$V_6$-$Y_7$-$I_8$-$P_9$-$X_4$-$X_5$-$R_{12}$-$P_{13}$-$P_{14}$-$H_{15}$-$P_{16}$-$X_6$-$X_7$-CT (SEQ ID NO:94)     (Formula B')

In these formulas,

NT is the free N-terminus of amino acid residue $X_1$ or the modified N-terminal amino group thereof, and CT is the free C-terminal carboxyl group of the C-terminal amino acid of the peptide (—COOH), the modified C-terminal carboxyl group thereof, or a peptide having preferably 2 to 6 amino acid residues with a free or modified C-terminus. CT is preferably a dipeptide, particularly preferably having one of the following amino acid sequences: RF (Arg-Phe), RL (Arg-Leu), RC (Arg-Cys), RK (Arg-Lys) or RR (Arg-Arg), and with a free or modified C-terminus.

In a peptide of general Formula A', B' or C' according to the invention, at least the N-terminus of amino acid residue $X_1$ or the C-terminus of the peptide is preferably modified.

Further preferred peptides of general Formula A', B' and C' according to the invention have an amino acid sequence according to any of general Formulas 1' to 10', which the individual variable amino acid residues $X_1$ to $X_4$ and $N_2$, and NT and CT are as defined above, and the remaining amino acid residues correspond to the IUPAC one-letter code:

NT-$X_1$-W-$X_2$-$X_3$-P-V-Y-I-P-$X_4$-R-R-P-P-H-P-CT (SEQ ID NO:109)     (Formula 1')

NT-$X_1$-W-$X_2$-$X_3$-P-V-Y-I-P-$X_4$-P-R-P-P-H-P-CT (SEQ ID NO:110)     (Formula 2')

NT-$X_1$-$N_2$-$X_2$-$X_3$-P-V-Y-I-P-$X_4$-R-R-P-P-H-P-CT (SEQ ID NO:111)     (Formula 3')

NT-$X_1$-R-$X_2$-$X_3$-P-V-Y-I-P-$X_4$-P-R-P-P-H-P-CT (SEQ ID NO:112)     (Formula 4')

NT-X$_1$-N$_2$-X$_2$-X$_3$-C-V-Y-I-P-X$_4$-P-R-P-P-H-P-CT
(SEQ ID NO:113)  (Formula 5')

NT-X$_1$-N$_2$-X$_2$-X$_3$-R-V-Y-I-P-X$_4$-P-R-P-P-H-P-CT
(SEQ ID NO:114)  (Formula 6')

NT-X$_1$-N$_2$-X$_2$-X$_3$-P-V-Y-R-P-X$_4$-P-R-P-P-H-P-CT
(SEQ ID NO:115)  (Formula 7')

NT-X$_1$-N$_2$-X$_2$-X$_3$-P-V-Y-I-P-X$_4$-P-R-P-C-H-P-CT
(SEQ ID NO:116)  (Formula 8')

NT-X$_1$-N$_2$-X$_2$-X$_3$-P-V-Y-I-P-X$_4$-P-R-P-P-H-C-CT
(SEQ ID NO:117)  (Formula 9')

NT-X$_1$-N$_2$-X$_2$-X$_3$-P-V-Y-I-P-X$_4$-P-R-P-P-H-P-R-R
(SEQ ID NO:118)  (Formula 10')

A "modification" of the N-terminal amino group or the C-terminal carboxyl group within the context of the invention is understood to mean that the amino group and/or the carboxyl group are modified, for example, reduced or substituted.

NT therefore represents the free N-terminus of amino acid X$_1$ or a modification of the N-terminal amino group (which replaces the N-terminal amino group of amino acid X$_1$ with NT) with the general formula NR$_1$R$_2$. In one alternative, the N-terminus of X$_1$ is unmodified (free), and therefore, in the general formula NT=NR$_1$R$_2$, residues R$_1$ and R$_2$ are hydrogen. In a further alternative, the N-terminus of X$_1$ is modified, in which NT=NR$_1$R$_2$, in which R$_1$ and R$_2$ are selected independently of one another, and residues R$_1$ and R$_2$ are preferably selected from the following groups:

(i) straight-chain, branched, cyclic and heterocyclic alkyl groups, preferably methyl, ethyl, n-propyl, isopropyl, n-butyl, isobutyl and cyclohexyl;

(ii) straight-chain, branched, cyclic and heterocyclic alkanoyl groups, preferably acetyl, methanoyl (formyl), propionyl, n-butyryl, isobutyryl, pentanoyl, hexanoyl and cyclohexanoyl;

(iii) reporter groups, preferably fluorescent dyes (preferably fluorescein, Alexa488) and biotin;

(iv) a linker for linking with the modification of the C-terminus of the peptide of general formula COR$_3$ (defined below) for forming a cyclic peptide, preferably based on guanidine, ethylene glycol oligomers, 2,4-diaminobutyric acid, 2,3-diaminopropionic acid, 2,2'-diaminopimelic acid, desmosine or isodesmosine;

(v) linkers for coupling a further peptide (Y$_2$) via a specific chemical or enzymatic reaction, preferably based on iodine, bromine or chloroalkanoic acids (e.g. iodoacetic acid) or maleimide for coupling to a thiol-containing peptide or another reactive group (e.g. amino group, thiol group) for coupling a second peptide or peptide derivative (e.g. as an active ester, aldehyde or thioester) as carrier proteins, and (vi) linkers analogous to (v), to which another peptide or peptide derivative Y$_2$ is coupled.

Preferred N-terminal modifications in a peptide according to the invention are acetylation, formylation and guanidination of the N-terminus. The N-terminus of a peptide according to the invention is particularly preferably guanidinated. The N-terminus is most preferably tetramethyl guanidinated.

CT represents the free C-terminal carboxyl group of the C-terminal amino acid (—COOH) or a modified C-terminal carboxyl group of a peptide according to the invention. The modified C-terminal carboxyl group CT preferably has the general formula COR$_3$ (R$_3$ replaces the hydroxyl group of the last amino acid) or Y$_1$—COR$_3$. In this connection Y$_1$ is an additional, preferably neutral polar or positively charged amino acid residue, particularly preferably leucine, arginine or glutamine, or a peptide, preferably having two to six amino acids, particularly preferably two to four amino acid residues, preferably a dipeptide having the sequence X$_6$X$_7$, which preferably contains at least one neutral polar or positively charged amino acid residue, which is preferably selected from leucine and arginine. Particularly preferred dipeptides Y$_1$ are selected from RI (Arg-Ile), RL (Arg-Leu), RV (Arg-Val), RC (Arg-Cys) and RR (Arg-Arg).

A preferred C-terminal modification of a peptide according to the invention is preferably selected from:

(i) carboxyl (R$_3$ is a free hydroxyl group), esters (R$_3$ is an alkoxy group, preferably methoxy, ethoxy, propoxy, iso-propoxy or butoxy), amides (R$_3$ is an amine, preferably alkylamine, dialkylamine, methylamine, ethylamine, dimethylamine or cyclohexylamine) and imides (R$_1$ is an amine, to which a further acid group, particularly the C-terminus of another peptide, e.g., as listed in connection with Y$_2$, or an acid group of a polymer or of a carrier is bonded);

(ii) linkers that bond the N-terminus of the peptide NT to the C-terminus, forming a cyclic peptide;

(iii) C-terminal modifications of general formula COR$_3$ in which R$_3$ is an additional, branched amino acid in order to form a dimer structure or oligomer structure, particularly selected from lysine, hydroxylysine, ornithine, 2,4-diaminobutyric acid, 2,3-diaminopropionic acid, 2,2'-diaminopimelic acid, desmosine, isodesmosine and peptides (preferably having 2-4 amino acids), which contain a combination of the aforementioned amino acids;

(iv) linkers for coupling a further peptide (Y$_2$) via a specific chemical or enzymatic reaction, preferably based on iodo-, bromo- or chloroalkanoic acids (e.g. iodoacetic acid) or maleimide for coupling to a thiol-containing peptide or another reactive group (e.g. amino group, thiol group) for coupling a second peptide or peptide derivative (e.g. as an active ester, aldehyde or thioester) as a carrier protein; and (v) linkers similar to (iv), to which another peptide or peptide derivative Y$_2$ is coupled.

In this way, C-terminal peptide derivatives can be obtained as esters (R$_3$=alkoxy), amides (R$_3$=amine, e.g., —NH$_2$ or imine, e.g. —NHC$_3$H$_7$) or imides, or as a peptide which has been extended by additional amino acids selected from Pro, Ile, Arg, and likewise modified at the C-terminus as ester, amide or imide. Additional peptide derivatives can be formed by modification of the N-terminal or C-terminal ends of the peptides. These modifications can be an additional alkyl group or alkanoyl group (either straight-chain or branched, cyclic or heterocyclic) or an additional guanidino group or an additional macromolecule or a reporter residue, for example, which can be linked either permanently or via a bond that can be cleaved under certain conditions (such as disulfide bridges or acid-labile linkers).

The C-terminus is preferably modified by means of thioester synthesis followed by substitution with primary amines.

The peptides according to the invention are derived from native apidaecin 1b (according to SEQ ID No. 2), in which at least one and preferably a maximum of 10 amino acids of the native sequence have been exchanged for another amino acid (substituted). A peptide according to the invention thus preferably has an amino acid sequence in which substitution in relation to SEQ ID No. 2 is carried out in at least one of positions 2, 5 to 9 and 13 to 16 of SEQ ID No. 2. A peptide according to the invention particularly preferably has an amino acid sequence in which substitution in relation to SEQ ID No. 2 is carried out in at least one of positions 2, 5 and 13 to 16 of SEQ ID No. 2, most preferably at positions 2 and 13. The peptide according to the invention particularly preferably comprises an amino acid sequence in which, as compared with SEQ ID No. 2,
- a non-polar amino acid residue, preferably an aromatic amino acid residue having 6 to 15, preferably 8 to 15, carbon atoms in the side chain, a positively charged amino acid residue, an amino acid residue containing a thiol group or an amino acid residue containing a selenol group, preferably selected from arginine, lysine, cysteine and tryptophan, most preferably tryptophan, is located in position 2, and/or
- a positively charged amino acid residue, an amino acid residue containing a thiol group or an amino acid residue containing a selenol group, preferably a positively charged amino acid residue, particularly preferably arginine, is located in at least one of positions 5 to 9 or 13, 14 and 16, preferably in at least one of positions 5, 13, 14 and 16, particularly preferably in position 13, and/or
- a positively charged, non-aromatic amino acid residue, an amino acid residue containing a thiol group or selenol group or an amino acid residue containing a selenol group is located in position 15.

A peptide according to the invention particularly preferably has an amino acid sequence in which substitution with cysteine or tryptophan takes place in position 2 in relation to SEQ ID No. 2, and/or at least one substitution with cysteine, lysine or arginine takes place in at least one of positions 5 and 13 to 16 of SEQ ID No. 2. A peptide according to the invention preferably has an amino acid sequence which additionally contains ornithine in position 1, in contrast to SEQ ID No. 2.

Surprisingly, peptides according to the invention, particularly those having the aforementioned substitutions in positions 2, 13, 14 and/or 18 of SEQ ID No. 2 (especially N2W, P13R, P14C and L18), exhibit a clear increase in activity in relation to *Pseudomonas aeruginosa*, and even in relation to the gram-positive bacterium *Staphylococcus aureus* (as compared with apidaecin 1b). The antimicrobial effect also occurs with physiological salt concentrations.

In a further embodiment, the peptide has an amino acid sequence in which at least one of the following substitutions takes place in relation to SEQ ID No. 2:

$N_2 \rightarrow$ amino acid with an alcoholic hydroxyl group in the residue; amino acid having a positive or neutral side chain with the exception of arginine;

$X_2 \rightarrow$ amino acid with a non-polar residue; amino acid containing a thiol group or selenol group in the residue; aromatic amino acid; amino acid containing an alcoholic hydroxyl group in the residue;

$P_5 \rightarrow$ aliphatic amino acid without a carboxyl group, with the exception of alanine; aromatic amino acid; and/or $V_6 \rightarrow$ aromatic amino acid; heterocyclic amino acid, amino acid with a positive residue; amino acid containing a thiol group or selenol group in the residue.

Particularly preferred peptides according to the invention contain one of the amino acid sequences according to SEQ ID Nos. 9 to 43 from Table 2, one of the amino acid sequences according to SEQ ID Nos. 9 to 43 with a modified, preferably guanidinated or acylated, N-terminus and/or with a modified, preferably amidated, C-terminus.

TABLE 2

| SEQ ID No. | Amino Acid Sequence |
|---|---|
| 9 | GWNRPVYIPRPRRPHP |
| 10 | GWNRPVYIPRPRRPHPRL |
| 11 | GWNRPVYIPRPRRPHPRI |
| 12 | GWNRPVYIPQPRRPHP |
| 13 | GWNRPVYIPQPRRPHPRL |
| 14 | GWNRPVYIPQPRRPHPRI |
| 15 | GWNRPVYIPQPRPPHPRL |
| 16 | GRNRPVYIPQPRPPHPRL |
| 17 | GNNRCVYIPQPRPPHPRL |
| 18 | GNNRRVYIPQPRPPHPRL |
| 19 | GNNRPVYRPQPRPPHPRL |
| 20 | GNNRPVYIPQPRRPHPRL |
| 21 | GNNRPVYIPQPRPCHPRL |
| 22 | GNNRPVYIPQPRPPHCRL |
| 23 | GNNRPVYIPQPRPPHPRR |
| 24 | GNNRPVYIPRPRRPHPRL |
| 25 | OWNRPVYIPRPRRPHPRI |
| 26 | OWNRPVYIPRPRRPHPRL |
| 27 | OWNRPVYIPRPRRPHPOI |
| 28 | OWNRPVYIPRPRRPHPOL |
| 29 | GWNRPVYIPRPRRPHPRC |
| 30 | GWNRPVYIPRPRRPHPRC |
| 31 | GWNRPVYIPQPRRPHPRC |
| 32 | GWNRPVYIPQPRRPHPRC |
| 33 | GWNRPVYIPQPRPPHPRC |
| 34 | GRNRPVYIPQPRPPHPRC |
| 35 | GNNRRVYIPQPRPPHPRC |
| 36 | GNNRPVYRPQPRPPHPRC |
| 37 | GNNRPVYIPQPRRPHPRC |
| 38 | GNNRPVYIPQPRPPHPRC |
| 39 | GNNRPVYIPRPRRPHPRC |
| 40 | OWNRPVYIPRPRRPHPRC |
| 41 | OWNRPVYIPRFRFPHPRC |
| 42 | OWNRPVYIPRPRRPHPOC |
| 43 | OWNRPVYIPRPRRPHPOC |
| 44 | ONNRPVYIPRPRPPHPRR |
| 45 | OWNRPVYIPRPRPPHPRL |
| 46 | ONNRFVYIPRPRRPHPRL |
| 47 | OWNRPVYIPRPRRPHPRL |

TABLE 2-continued

| SEQ ID No. | Amino Acid Sequence |
|---|---|
| 48 | ONNRPVYIPRPRRPHPRL |
| 49 | OWNRPVYIPRPRRPHPRI |

Particularly preferred peptides according to the invention contain one of the amino acid sequences from Table 2, in which the C-terminus of the peptide is also amidated and/or the N-terminus is guanidinated and/or tetramethyl guanidinated (indicated in Tables 3 and 6 by "gu"). Preferred examples of peptides amidated in this manner are listed in Table 3:

TABLE 3

| SEQ ID No. | Amino Acid Sequence |
|---|---|
| 50 | GWNRPVYIPRPRRPHPRL-NH$_2$ |
| 51 | GWNRPVYIPRPRRPHPRI-NH$_2$ |
| 52 | GWNRPVYIPQPRRPHPRL-NH$_2$ |
| 53 | GWNRPVYIPQPRRPHPRI-NH$_2$ |
| 54 | GWNRPVYIPQPRPPHPRL-NH$_2$ |
| 55 | GRNRPVYIPQPRPPHPRL-NH$_2$ |
| 56 | GNNRCVYIPQPRPPHPRL-NH$_2$ |
| 57 | GNNRRVYIPQPRPPHPRL-NH$_2$ |
| 58 | GNNRPVYRPQPRPPHPRL-NH$_2$ |
| 59 | GNNRPVYIPQPRRPHPRL-NH$_2$ |
| 60 | GNNRPVYIPQPRPCHPRL-NH$_2$ |
| 61 | GNNPRVYIPQPRPPHCRL-NH$_2$ |
| 62 | GNNRPVYIPQPRPPHPRR-NH$_2$ |
| 63 | GWNRPVYIPQPRPPHPRL-NH$_2$ |
| 64 | GNNRPVYIPRPRRPHPRL-NH$_2$ |
| 65 | OWNRPVYIPRPRRPHPRI-NH$_2$ |
| 66 | OWNRPVYIPRPRRPHPRL-NH$_2$ |
| 67 | OWNRPVYIPRPRRPHPOI-NH$_2$ |
| 68 | OWNRPVYIPRPRRPHPOL-NH$_2$ |
| 69 | GWNRPVYIPRPRRPHPRC-NH$_2$ |
| 70 | GWNRPVYIPRPRRPHPRC-NH$_2$ |
| 71 | GWNRPVYIPQPRRPHPRC-NH$_2$ |
| 72 | GWNRPVYIPQPRRPHPRC-NH$_2$ |
| 73 | GWNRPVYIPQPRPPHPRC-NH$_2$ |
| 74 | GRNRPVYIPQPRPPHPRC-NH$_2$ |
| 75 | GNNRRVYIPQPRPPHPRC-NH$_2$ |
| 76 | GNNRPVYRPQPRPPHPRC-NH$_2$ |
| 77 | GNNRPVYIPQPRPPHPRC-NH$_2$ |
| 78 | GNNRPVYIPQPRPPHPRC-NH$_2$ |
| 79 | GNNRPVYIPRPRRPHPRC-NH$_2$ |

TABLE 3-continued

| SEQ ID No. | Amino Acid Sequence |
|---|---|
| 80 | OWNRPVYIPRPRRPHPRC-NH$_2$ |
| 81 | OWNRFVYIPRPRRPHPRC-NH$_2$ |
| 82 | OWNRPVYIPRPRRPHPOC-NH$_2$ |
| 83 | OWNRPVYIPRPRRPHPOC-NH$_2$ |
| 84 | gu-ONNRPVYIPRPRPPHPRR-OH |
| 85 | gu-OWNRPVYIPRPRPPHPRL-OH |
| 86 | gu-ONNRPVYIPRPRPPHPRL-OH |
| 87 | gu-OWNRPVYIPRPRRPHPRL-OH |
| 88 | gu-ONNRPVYIPRPRRPHPRL-NH$_2$ |
| 89 | gu-OWNRPVYIPRPRRPHPRL-NH$_2$ |
| 92 | gu-ONNRPVYIPRPRPPHPRL-NH$_2$ |
| 93 | gu-ONNRPVYIPRPRPPHPRL-OH |

The N-terminus of a peptide according to the invention from Table 2 is particularly preferably guanidinated (hereinafter NT="guan" or "gu"). Preferred peptides according to the invention having a guanidinated N-terminus comprise an amino acid sequence according to any of SEQ ID Nos. 44 to 49 in which the C-terminus of the peptide is preferably also amidated.

All of the natural amino acids, unnatural amino acids or amino acid derivatives (e.g. imino acids) which form the peptides or peptide derivatives according to the invention may be present in either the L configuration or the D configuration. However, unless otherwise specified, the building blocks in the sequence are preferably in the L configuration.

The modifications of the N- and C-termini allow the peptides to be coupled to other groups, for example, to other amino acid sequences (potentially creating multimeric peptides or proteins) or to other biomolecules which function as carriers or labels, for example $Y_2$, via NT. In one specific embodiment, the molecule acts as a carrier for fighting bacterial infection in mammalian cells, or for transporting the antibacterial peptide and peptide derivative into bacteria that the antibacterial peptide alone cannot penetrate (e.g. gram-positive bacteria). Examples of such cell-penetrating peptides (CPP) include penetratins, Tat peptides, model amphipathic peptides and transportans. In addition, the site of the infection can be detected by the coupled structure (target molecule), and as a result, the antibiotic substance can be brought to the location of the (bacterial) cell in order to fight it. Such target molecules include molecules that are known to bind to lipopolysaccharide (LPS) molecules, which form the exterior of the gram-negative bacteria. Known compounds for this application include anchor peptides, such as the AcmA motif of *lactobacillus* or an antibody directed against lipopolysaccharide. The latter variant is preferred since it also has an intrinsic antibiotic effect, and can therefore be used to enhance the activity of the peptides according to the invention.

Coupling a cell-penetrating peptide sequence, such as penetratin, allows the activity against gram-negative and gram-positive bacteria to be enhanced, and/or allows the spectrum of activity against other gram-positive and gram-negative bacteria to be expanded, while at the same time transfecting the antimicrobial peptides into mammalian cells in order to reach bacteria, fungi or viruses that are hidden in these cells. The coupling of the penetratin via a thioether bridge is a feature of this invention. In this case, the C-terminus of the penetratin is extended by one cysteine, and is coupled at the N-terminal to the antimicrobial peptide marked with iodoacetic acid.

The term "peptide", as used herein, refers to a sequence of amino acids that are linked via a peptide bond, in which the amino acids are preferably selected from the twenty proteinogenic amino acids, and in which the amino acids may be present in the L configuration or the D configuration, or in the case of isoleucine and threonine, in the D-allo configuration (merely an inversion of one of the two chiral centers). This term also encompasses peptide derivatives that have been modified by substitution and/or modification of one or more amino acid residues with chemical groups, with these chemical groups being amino acid residues other than the natural, protein-forming amino acid residues, such as non-proteinogenic α-amino acids, β-amino acids or peptides with a modified backbone. The term "modified backbone" means that at least one peptide bond is chemically modified, i.e., is replaced by a bond that cannot be cleaved under physiological conditions, and which cannot be cut by endoproteases.

The uncleavable bond is preferably a modified peptide bond, such as a reduced peptide bond, an alkylated amide bond or a thioamide bond, for example. A reduced amide bond is a peptide bond in which the carbonyl group (C=O) is reduced to a hydroxyl group (HCOH) or a methylene group ($CH_2$). An alkylated amide bond is a peptide bond that is alkylated on either the nitrogen (N-alpha) atom or the carbon (C-alpha) atom. The alkyl residue preferably has 1 to 3 carbon atoms. One example of this is N-methylation.

The term modified backbone also encompasses other groups which are suitable for forming a covalent bond with both the COOH group of the preceding amino acid residue and the $NH_2$ group of the subsequent amino acid residue, and which therefore do not necessarily maintain the peptide backbone structure, for example, sugar amino acid dipeptide isosteres, azapeptides, 6-homopolymers, gamma peptides, depsipeptides (ester bridges in the backbone), Y-lactam analogues, oligo(phenylene-ethylene)s, vinylogenic sulfonyl peptides, poly-N-substituted glycines or oligocarbamates. Modifications of the backbone are preferred at positions that are susceptible to enzymatic degradation, particularly in the area of arginines and lysines. Here, the peptide bond is preferably replaced with a bond that cannot be cleaved by proteases. This uncleavable bond is preferably selected from the group of reduced amide bonds, alkylated amide bonds or thioamide bonds.

The peptides according to the invention are preferably linear. Alternatively, the peptides according to the invention are cyclical, in which case the first (N-terminus) and the last amino acid (C-terminus) are preferably linked via a peptide bond or a linker. The invention also comprises cyclizations between a side chain (e.g. lysine) and the C-terminus of the peptide, a side chain (e.g. glutamic acid or asparaginic acid) and the N-terminus of the peptide or between two side chains (e.g. lysine and glutamic acid or asparaginic acid).

Methods for producing the peptides according to this invention are additional features of the invention.

The peptides or peptide derivatives thereof according to the invention can be produced either synthetically or, where applicable, recombinantly by conventional methods. The peptides or peptide derivatives of this invention are preferably produced by conventional methods using the known synthesis techniques, such as those described by Merrifield. Alternatively, the peptides described in this invention are produced by recombinant techniques, in which a DNA fragment that contains a nucleic acid sequence encoded for one of the above-described peptides is cloned and then expressed, e.g. in a microorganism or a host cell. The encoding nucleic acid sequences can be produced synthetically or obtained through side-specific mutagenesis of an existing nucleic acid sequence. The encoding sequence produced in this manner can be amplified from the RNA (or DNA) by known techniques using suitably produced primers in a polymerase chain reaction (PCR). After purification, for example by means of agarose gel electrophoresis, the PCR product is ligated in a vector, and finally, the host cell is transformed with the corresponding recombinant plasmid. Recombinant techniques are known for various host cells, for example, E. *Coli, Bacillus, Lactobacillus, Streptomyces*, mammalian cells (e.g. CHO (Chinese hamster ovary) or COS-1 cells), yeast cells (e.g. *Saccharomyces, Schizophyllum*), insect cells or viral expression systems (e.g. Baculovirus system). After conventional recombinant preparation, the peptides of this invention can be isolated from the host cells, either through classic cell fusion techniques or from the cell medium through conventional methods, e.g. liquid chromatography, particularly affinity chromatography. The peptide according to the invention can be expressed as an individual peptide or as an oligomer. These oligomers may contain multiple peptide sequences that are linked via the N-terminus or the C-terminus, or may even contain one N-terminal tag or C-terminal tag which permits easier purification of the recombinant peptides or protein constructs. Conventional molecular-biological techniques and side-specific mutagenesis may be used to further modify the sequence and thereby obtain the desired non-native peptide sequences. These recombinant techniques have already been used with many antimicrobial peptides, including apidaecin (see, e.g., Maeno M et al. 1993).

It is also possible to introduce non-naturally occurring amino acids into the peptides through genetic techniques (Noren C et al. 1989; Ellman J et al. 1991).

The peptides can then be isolated from the host cell culture or the in vitro translation system. This can be achieved through standard techniques of protein purification and isolation, which are part of the prior art. Such techniques may include immune absorption or affinity chromatography, for example. It is also possible to provide the peptides with a tag during synthesis (e.g. histidine tag), which permits rapid bonding and purification. The tag can then be split off enzymatically in order to obtain the active peptide sequence.

If the peptide cannot itself be encoded or expressed, but is very similar to an encodable or expressible peptide, this method can be applied first to the similar peptide, which can then be chemically or enzymatically converted in one or more steps to the desired peptide or peptidomimetic.

The invention also comprises nucleic acids that encode for the peptides according to the invention, and preferably non-human host cells that contain a nucleic acid according to the invention. The host cells are preferably selected as described above, and do not include human embryonic stem cells.

The peptides according to the invention can be used individually, in combination, as multimers or as branched multimers. Logical combinations of the peptides according to the invention comprise dendrimers and concatamers in which the peptides according to the invention are linked to one another in series or via spacers, e.g., in the form of a peptide dimer or a peptide trimer, etc., by placing the individual peptides in series. Such a multimer can be composed of peptides or peptide derivatives having identical sequences or different sequences according to Formula A or B.

The modified peptides can also be coupled to a biocompatible protein, for example, human serum albumin, humanized antibodies, liposomes, micelles, synthetic polymers, nanoparticles and phages. Alternatively, multimers in which the peptides or peptide derivatives according to the invention are individually combined can be produced in the form of dendrimers or clusters in which three or more peptides are bonded to a center.

In one embodiment, several peptides can be produced as multimeric constructs or arrangements. For example, amino acids (e.g. Gly-Ser) or other spacers (linker peptides) based on amino acids or other chemical compounds can optionally be appended to the N-terminus or C-terminus in order to link two or more peptides with one another, or to couple these to a carrier. This arrangement can be in the form of one or more of the above-described synthetic peptides coupled to a carrier protein. Alternatively, an arrangement may contain multiple peptides, each expressed as a multiple antigenic peptide, optionally coupled to a carrier protein. In a further variant, the selected peptides are linked in sequence, and are expressed as a recombinant protein or as a polypeptide. In one embodiment, a plurality of peptides are linked in sequence, with or without amino acids between them as spacers (linker peptides), in order to obtain a larger recombinant protein. Alternatively, the recombinant protein can be fused to a carrier protein.

In another embodiment, the multimeric constructs contain at least two peptides, wherein one peptide is coupled via any amino acid to the other peptides. Any number of additional peptides can be appended to any number of additional amino acids of these peptides. In a further embodiment of a multimeric arrangement which contains at least two peptides, the second peptide or the additional peptides are coupled to a branched framework of the other peptides of the basic structure. Alternatively, each additional peptide is covalently bonded via the NT or CT group to another peptide in the arrangement.

In another embodiment of a multimeric construct or an arrangement having at least two peptides, at least one or more peptides are bonded to a carrier. In another embodiment, one or more of the stated peptides is a synthetic peptide that is fused to a carrier protein. A further alternative consists in combining several of the above-described peptides in sequence, with or without accompanying sequences, to form a linear polypeptide. The peptides or the polypeptide are either coupled to the same carrier, or different peptides can be coupled individually as peptides to one or to various immunologically inert carrier proteins.

Suitable carriers can be used to improve stability, administration or production, or to alter the functional spectrum of the peptides. Examples of suitable carriers include human albumin, polyethylene glycol or other biopolymers and/or other naturally or non-naturally occurring polymers. In one embodiment, the main component is preferably a protein or other molecule that is capable of increasing the stability of the peptide. An experienced person can easily select a suitable coupling unit.

In yet another embodiment, the peptides are arranged in the form of a multiple antigenic peptide (MAP). This system uses a central unit comprising lysine residues, to which multiple copies of the same peptide according to the invention are synthesized. Each MAP contains multiple copies of one or more of the peptides according to the invention. One embodiment of an MAP contains at least three, and preferably four or more peptides. A person skilled in the an could easily produce any number of multimeric compounds according to the peptides identified in the above formula. All such multimeric arrangements and constructs are considered a feature of this invention. Additional combinations in the form of multimers can be produced on the surface of particles, in which case the peptides or peptide derivatives are present on the surface thereof. The particles can then function as carriers for a peptide or peptide derivative, while at the same time acting as detectable markers. Multimers can be obtained, for example, by N-terminal biotinylation of the N-terminal end of the peptide chains or peptide derivative chains, followed by complex formation with Streptavidin. Since streptavidin is able to bind four biotin molecules or conjugates with high affinity, this method results in highly stable tetrameric peptide complexes. Multimers can be produced from identical or from different peptides or peptide derivatives according to the invention. The multimers according to the invention preferably contain two or more peptides or peptide derivatives in which each component contributes a certain portion to biocidal activity (target recognition, antimicrobial activity, purification).

The subject matter of this invention further comprises the use of the peptides or peptide derivatives described herein in the field of medicine or pharmaceuticals, e.g. for antibiotic treatment or in a composition with antimicrobial (particularly bactericidal) action. The peptide is preferably used medicinally as an antibiotic against gram-positive bacteria.

The subject matter of the invention further comprises the peptides according to the invention for use in medicine, as antibiotics, in disinfection or cleaning agents, as preservatives, or in packaging material. The peptide modified according to the invention is particularly well suited for the treatment of microbial, bacterial or fungal infections.

The subject matter of the invention further comprises the use of the peptides according to the invention for producing a pharmaceutical agent, particularly an antibiotic, especially for use in the treatment of microbial infections, e.g., with bacteria, viruses and fungi.

The subject matter of the invention further comprises the use of the peptides according to the invention in pharmaceuticals research or in screening processes, preferably in a screening process designed to identify substances with antimicrobial, bactericidal or antimycotic action.

A suitable screening process of this type designed to identify a substance which can be expected to have antimicrobial, bactericidal or antimycotic action comprises:
  (i) performing a competitive assay with:
    (a) a microorganism that is sensitive to a peptide according to the invention;
    (b) a peptide according to the invention and
    (c) at least one substance to be tested (test substance) by placing (a) in contact with (b) and (c); and
  (ii) selecting a test substance that will force the competitive bonding of the peptide to the microorganisms.

The subject matter of this invention further comprises pharmaceutical compositions containing one or more peptides according to the invention, or the multimeric constructs thereof, independently of the presence of other pharmaceutically active compounds.

A further feature of this invention is the use of the peptides according to the invention as a pharmaceutical agent and/or in producing an active ingredient that can be used as an antibiotic.

The peptides according to the invention can also be used individually in pharmaceutical products. Alternatively, one or more modified peptides, as described above, can be fused or conjugated to another compound in order to enhance the pharmacokinetics or bioavailability thereof, without triggering an immune response. Any number of individual peptides or multimeric constructs may be combined with one another in order to produce an individual composition.

A pharmaceutical composition according to the invention contains a therapeutically active quantity of one or more peptides according to the invention or the multimeric constructs thereof. Once combined, the pharmaceutical composition according to the invention can be administered directly to the subject in order to treat microbial (particularly bacterial) infections. A therapeutically active quantity of a composition according to the invention is administered to the subject to be treated for this purpose.

The pharmaceutical compositions according to the invention are intended for treating infection in mammals, including humans, infected with bacteria or fungi. At least one, or alternatively several peptides according to the invention or the multimeric constructs thereof can be combined to produce an antimicrobially (particularly antibacterially or fungicidally) active composition having a pharmacologically acceptable carrier or other components. For the use of such a composition, the selected peptide is preferably produced through synthetic or recombinant methods, as described above.

The pharmaceutical composition according to the invention is directly administered locally or systemically, preferably orally, parenterally, intraperitoneally, intravenously, intramuscularly, pulmonally or interstitially into the tissue.

The pharmaceutical composition according to the invention can further contain suitable and pharmaceutically acceptable carriers, cutting agents, buffers or solvents, and may be in the form of a capsule, tablet, lozenge, coated tablet, pill, drops, suppository, powder, spray, vaccine, salve, paste, cream, inhalant, plaster, aerosol, etc. Suitable pharmaceutically acceptable vehicles include solvents, cutting agents or other liquid binders such as dispersion or suspension media, surface-active agents, isotonic pharmaceutical ingredient, thickeners or emulsifiers, preservatives, encapsulating agents, solid binders or lubricants, depending on what is most suitable for the respective dosing and is at the same time compatible with the peptide, peptide derivative or peptide conjugate.

The pharmaceutical composition according to the invention therefore preferably contains a pharmaceutically acceptable carrier. The term "pharmaceutically acceptable carrier" in this case also refers to a carrier for administering the therapeutic composition, such as antibodies or polypeptides, genes or other therapeutic agents, for example. The term refers to any pharmaceutical carrier which does not itself trigger the production of antibodies that might be harmful to the individual to whom the preparation has been administered, and are not unreasonably toxic. Suitable "pharmaceutically acceptable carriers" include large macromolecules that degrade slowly, for example, proteins, polysaccharides, polylactonic acids, polyglycolic acids, polymeric amino acids, amino acid copolymers and deactivated virus constituents. Such carriers are well known to a person skilled in the art.

Salts of the peptides according to the invention are produced by known methods, which typically means that the peptides according to the invention, or the peptide conjugates or conjugates thereof, are mixed with a pharmaceutically acceptable acid to form an acid salt or with a pharmaceutically acceptable base to form a basic salt. Whether an acid or a base is pharmaceutically acceptable can be readily determined by a person skilled in the art based upon the application and the preparation. Thus, for example, not all acids and bases that are acceptable for ex vivo applications can also be transferred to therapeutic preparations. Based upon the respective application, pharmaceutically acceptable acids may be either organic or inorganic in nature, e.g., formic acid, acetic acid, propionic acid, lactic acid, glycolic acid, oxalic acid, pyruvic acid, succinic acid, maleic acid, malonic acid, cinnamic acid, sulfuric acid, hydrochloric acid, hydrobromic acid, nitric acid, perchloric acid, phosphoric acid and thiocyanic acid, which form ammonium salts with the free amino groups of peptides and functionally equivalent compounds. Pharmaceutically acceptable bases that form carboxylates with free carboxylic acid groups of the peptides and functionally equivalent compounds contain ethylamine, methylamine, dimethylamine, triethylamine, isopropylamine, diisopropylamine and other mono-, di- and trialkylamines and arylamines. Pharmaceutically acceptable solvents are also included.

Pharmaceutically acceptable salts may be used in pharmaceutical compositions according to the invention, for example, salts of mineral acids, such as hydrochlorides, hydrobromides, phosphates, sulfates, etc.; but also salts of organic acids, such as acetates, propionates, malonates, benzoates, etc.

Pharmaceutically acceptable carriers in the pharmaceutical compositions according to the invention further comprise liquids, for example water, salt water, glycerol and ethanol. In addition, pharmaceutical compositions according to the invention may contain auxiliary agents, such as moistening agents or emulsifiers, pH buffering substances, and similar compounds. Typically, the pharmaceutical compositions according to the invention are prepared either in liquid form or as a suspension for injection, and solid forms for dissolution or suspension in carrier liquids prior to injection are also possible. The definition of a "pharmaceutically acceptable carrier" also includes liposomes.

For therapeutic treatment, peptides according to the invention or peptide conjugates thereof, as described above, can be produced and administered to a subject requiring them. The peptide or peptide conjugate can be administered to a subject in any suitable form, preferably as a pharmaceutical composition that is adapted to the dosage form and is present in an appropriate dosage for the desired treatment.

The pharmaceutical compositions of this invention can contain additional active compounds, for example, conventional antibiotics (e.g., vancomycin, streptomycin, tetracycline, penicillin) or other antimicrobially active compounds, such as fungicides, e.g. intraconazol or myconazol. Other compounds that relieve symptoms associated with the infection, such as fever (salicylic acid) or rash, may also be added.

In addition to the therapeutic use for the treatment of infections, the peptides or peptide derivatives according to the invention may also be used in disinfecting agents or cleaning agents (e.g., a bactericidal composition), which can be used for disinfecting or cleaning surfaces or objects, particularly for the purpose of preventing or removing biofilms. Another area of application includes packaging, in which peptides according to the invention are bonded to packaging material or can be incorporated therein, or as preservative agents for other materials that can be readily degraded by microorganisms. The peptides or peptide derivatives according to the invention are particularly well suited for the packaging of foods since they do not produce a toxic effect either on contact or when ingested.

A further feature of this invention is a method for treating mammals that are infected with microbes (particularly bacteria or fungi), including the administration of an effective, therapeutically active quantity of the pharmaceutically active composition according to the invention.

The term "therapeutically active quantity" used herein refers to the quantity of a therapeutic agent, i.e., of a peptide, peptide derivative or peptide conjugate according to the invention, which is capable of reducing or even preventing the propagation and colony formation of the bacteria, or of achieving a measurable therapeutic and/or prophylactic result. The effect can be ascertained, for example, for biopsies in culture, by testing bacterial activity or by some other suitable method for assessing the extent and the degree of a bacterial infection. The precise quantity that is effective for a subject is based upon the size and health status of the subject, the nature and the extent of the disease and the therapy or the combination of multiple therapies that are chosen for the treatment. In particular, the pharmaceutical compositions according to the invention can be used for reducing or preventing bacterial infections and/or accompanying biological or physical symptoms (e.g. fever). Methods for determining the initial dosage by a medical professional are part of the prior art. The established dosages must be safe and effective.

The quantity of a peptide according to the invention that is required for an antibacterially effective dose can be determined based on the pathogen that triggers the infection, the severity of the infection, and the age, weight, sex, general physical condition, etc. of the patient. The quantity of the peptide according to the invention that is required for effective antibacterial and antimycotic action without notable side effects is dependent upon the pharmaceutical formulation that is used and upon the optional presence of additional constituents such as antibiotics, antimycotics, etc. For the areas of application according to the invention, an effective dose may be between 0.01 nmol/kg and 50 nmol/kg, and is preferably between 0.2 nmol/kg and 10 nmol/kg of the peptide, peptide derivative or peptide conjugate in the individual being treated.

Initial doses of the peptides, peptidomimetics, multimers, peptide conjugates or peptidomimetic conjugates according to the invention can optionally be administered in multiple doses. The frequency of doses is dependent on the above-described factors and is preferably between one and six doses per day over a treatment period of approximately three days to a maximum of one week.

In a further embodiment, the compounds are administered pulmonally in a specific quantity, e.g., through an inhaler, a nebulizer, an aerosol spray or a dry powder inhaler. Suitable formulations may be produced by known methods and techniques. Transdermal or rectal administration may be used in some cases, as can ocular administration.

It may be advantageous to administer the substances according to the invention more effectively through advanced drug delivery or targeting methods. For instance, if it is desirable to avoid the digestive tract, the form for administration may contain any substance or mixture that increases bioavailability. This can be achieved, for example, by reducing degradation, e.g., by an enzyme inhibitor or an antioxidant. It is better for the bioavailability of the compound to be achieved by increasing the permeability of the absorption barrier, in most cases the mucous membrane. Substances that facilitate permeation can act in several ways; some increase the fluidity of the mucous membrane, while others expand the interstices between the mucous membrane cells. Still others reduce the viscosity of the mucous on the mucous membrane. Preferred absorption accelerators include amphiphilic substances such as cholic acid derivatives, phospholipids, ethanol, fatty acids, oleic acid, fatty acid derivatives, EDTA, carbomers, polycarbophil and chitosan.

Indications for which the modified peptides or the conjugates or multimers thereof can be used include bacterial infections with both gram-positive and gram-negative bacteria, for example, *Escherichia coli, Enterobacter cloacae, Erwinia amylovora, Klebsiella pnewnoniae, Morganella morganii, Pseudomonas aeruginosac Salmonella typhimurium, Salmonella typhi, Shigella dysenteriae, Yerslnia enterocolitica, Acinerobacter calcoaceticuc Acinetobacter baumannii, Agrobacteriuon tumefaciens. Francisella tularensis, Legionella pneumophila, Pseudomonas syringae, Pseudomonas aeruginosa, Rhizobium meliloti, Haemophilus influenzae* and *Staphylococcus aureus.*

Below, the invention will be specified in greater detail in reference to the following embodiment examples and figures, without the invention being limited to these:

FIG. 1 shows the results of the substitution analysis of apidaecin 1b (GNNRPVYIPQPRPPHPRL—SEQ ID No. 2) with the amino acids indicated in the form of the one-letter code. Values of less than 1 indicate an enhancement of microbial activity. Values of greater than 1 indicate a deterioration in microbial activity. The left column shows the native sequence. The top line shows the substituents. The value of 0.55 directly below the C, for example, is a measure of the activity of the native apidaecin sequence that is substituted at position 1 with cysteine.

FIG. 2 shows a specific embodiment of the peptides described herein. Each peptide marked with X is more effective than native apidaecin and is particularly advantageous in relation to gram-positive bacteria.

FIG. 3 shows a permeabilization assay. *E. coli* BL21AI with apidaecin derivatives. Api88 corresponds to the peptide having SEQ ID No. 92; Api137 corresponds to the peptide having SEQ ID No. 93; Api1341 corresponds to the peptide having SEQ ID No. 89.

EXAMPLES

Example 1

Substitution Analysis by Means of Peptide Array

To optimize the antimicrobial activity of apidaecin 1b, a substitution analysis was carried out using this peptide (according to SEQ ID No. 2). The substitution library was synthesized by means of SPOT synthesis, and was analyzed for antibacterial activity against *Pseudomonas aeruginosa* by means of bioluminescence assay.

The SPOT synthesis of the peptide libraries was carried out on Whatman 50 filter paper (Sigma-Aldrich, Germany) measuring 19×29 cm by means of the Fmoc method and a SPOT synthesizer (Intavis AG, Germany) (according to Reineke U et al. 2001). The luminescence screening method that was used is based on the publication by Hilpert and Hancock (Hilpert, 2007). The peptides synthesized on the membrane were split off and the peptide spots were punched out of the peptide membrane using a hole punch, and were transferred to a 96-well microtiter plate (Corning, USA), after which 200 μL distilled water per well was added. The plate was sealed with aluminum foil (Biorad, Germany) and shaken lightly for 18 hours at RT. Each peptide of the array was thereby transferred to precisely one well in a microtiter plate, referred to as a master plate. The sealed master plates were stored at −20° C. The master plates were designed such that each row contains 10 peptides and two control samples (positive and negative).

In the second step, the actual screening was performed. For this purpose, an overnight culture (37° C., 225 rpm, 18 h) of a strain of luminescent bacteria (*P. aeruginosa*) was used. The overnight culture was diluted 100 times and allowed to grow to an optical density of 0.35 at 600 nm [OD600] (approx. 2 hours—logarithmic phase culture—Log C). The incubation suspension (4 vol. % Log C in 100 mM Tris-HCl buffer (pH 7.3) with 40 mM sterile filtered glucose) was then distributed to 96-well plates (VWR, Germany) that are suitable for luminescence, and incubated with a concentration series of the peptide library for 4 hours at 37° C. After incubation, luminescence measurement was performed using a luminometer (Thermo, Finland).

From the results of the substitution analysis, those peptide sequences that showed the greatest activity in the assay were selected. These peptides were synthesized by conventional means on a polymeric carrier, and were analyzed in terms of their antibacterial activity against *P. aeruginosa, E. coli* and *S. aureus* by means of MIC assay.

Example 2

Determining Minimum Inhibitory Concentrations and Growth Kinetics

The minimum inhibitory concentrations (MIC) of the peptides were determined in a double assay of triplicates using a positive control sample (gentamycin) and a negative control sample (0.9% NaCl solution), according to a modified protocol from Wiegand et al. (Wiegand, 2008).

For this purpose, the peptides were dissolved in water and were diluted in a double dilution series with 1/8 MH (eight-fold diluted Mueller-Hinton-Medium—2.6 g/L, Merck) in sterile 96-well, plates (Greiner Bio-One GmbH) in twelve dilution steps from 128 µg/mL to 62.5 ng/mL. Overnight cultures were adjusted using ⅛ MHB to approximately $1.5 \times 10^7$ colony forming units per mL. Of these, 50 µL of peptide solution per well was mixed with 50 µL bacteria solution each to obtain an initial concentration of 4×10 bacteria per well. After 20 hours of incubation at 37'C, the absorption was determined at 595 nm (microplate reader, Wallac Victor3, Perkin Elmer). The minimum inhibitory concentration was identified as the lowest peptide concentration at which no bacterial growth could be detected.

In the experiment, the antibacterial activity of the peptides according to the invention in relation to the following bacterial strains was analyzed: *Pseudomonas aeruginosa* PAO1 (wt strain), *Pseudomonas aeruginosa* DSM 9644, *Staphylococcus aureus* DSM 1104/ATCC 25923, *Staphylococcus aureus* ATCC 6247, *Escherichia coli* UB 1005 (F—, nalA37, metB1) and *Escherichia coli* ATCC25922. The following Table 4 shows the results of the test:

TABLE 4

Minimum inhibitory concentration in 1/8 MHB in µg/mL

| | | MIC [µg/mL] | | | Improvement over Native Sequence (SEQ No. 2) | |
| --- | --- | --- | --- | --- | --- | --- |
| SEQ ID No. | Peptide | P. aeruginosa PAO1 wt | E. coli UB1005 | S. aureus ATCC 25923 | P. aeruginosa PAO1 wt | E. coli UB1005 | S. aureus ATCC 25923 |
| 2* | GNNRPVYIPQPRPPHPRL-OH | 500 | 5 | >125 | 1 | 1 | 1 |
| 90* | GNNRPVYIPQPRPPHPRL-NH$_2$ | 250 | 1.25 | >125 | 2 | 4 | |
| 54 | GWNRPVYIPQPRPPHPRL-NH$_2$ | 64 | 1.25 | 63 | 8 | 4 | 4 |
| 55 | GRNRPVYIPQPRPPHPRL-NH$_2$ | 64-128 | 0.625 | 32 | 4-8 | 8 | 8 |
| 56 | GNNRCVYIPQPRPPHPRL-NH$_2$ | 125 | 10 | 31 | 4 | 1 | 8 |
| 57 | GNNRRVYIPQPRPPHPRL-NH$_2$ | 64 | 5 | 32 | 8 | 1 | 8 |
| 58 | GNNRPVYRPQPRPPHPRL-NH$_2$ | 64 | 0.313 | 63 | 8 | 16 | 4 |
| 59 | GNNRPVYIPQPRRPHPRL-NH$_2$ | 125 | 10 | 31 | 4 | 1 | 8 |
| 60 | GNNRPVYIPQPRPCHPRL-NH$_2$ | 250 | 20 | 16 | 2 | 0 | 16 |
| 61 | GNNRPVYIPQPRPPHCRL-NH$_2$ | 125 | 20 | 32 | 4 | 0 | 8 |
| 62 | GNNRPVYIPQPRPPHPRR-NH$_2$ | 125 | 1.25-2.5 | 125 | 4 | 2-4 | 2 |
| 63 | GWNRPVYIPRPRPPHPRL-NH$_2$ | 16-32 | 0.63 | 16 | 16-32 | 8 | 16 |
| 52 | GWNRPVYIPQPRRPHPRL-NH$_2$ | 64 | 5 | 4-8 | 8 | 1 | 31-64 |
| 64 | GNNRPVYIPRPRRPHPRL-NH$_2$ | 64 | 2.5 | 4 | 8 | 2 | 64 |
| 50 | GWNRPVYIPRPRRPHPRL-NH$_2$ | 32 | 2.5 | 2 | 16 | 2 | 128 |
| 91* | GNNDPVYIPQPRPPHPRL-NH$_2$ | 121.0 | >19.4 | >60.5 | 4 | <0.25 | |

*Comparative examples

The results show that the modifications (particularly N2W and/or P15R) significantly increase antimicrobial activity, particularly against *P. aeruginosa* and *S. aureus*.

The antibacterial activity of the peptides according to the invention against the following pathogenic bacteria strains of the gram-positive bacterium *S. aureus* and of *P. aeruginosa* was also analyzed:

TABLE 5

Antimicrobial activity against various pathogenic strains of *S. aureus*, and *P. aeruginosa* strains. MIC values were determined in triplicate in 1/8 MHB in µg/mL.

| SEQ ID No. | | S. aureus DSM 6247 | S. aureus DSM 1104/ ATCC 25923 | E. coli ATCC 25922 | P. aeruginosa PAO DSM 9644 | P. aeruginosa PAO1 wt |
|---|---|---|---|---|---|---|
| 2* | GNNRPVYIPQPRPPHPRL-OH | 256 | >125 | 2 | >256 | 500 |
| 90* | GNNRPVYIPQPRPPHPRL-NH$_2$ | 64 | >125 | 2 | n.d. | 250 |
| 52 | GWNRPVYIPQPRRPHPRL-NH$_2$ | 2 | 4-8 | 16 | 64 | 64 |
| 64 | GNNRPVYIPRPRRPHPRL-NH$_2$ | 2 | 4 | 8 | 32 | 64 |
| 50 | GWNRPVYIPRPRRPHPRL-NH$_2$ | 2 | 2 | 8 | 32 | 32 |

*Comparative examples, n.d.: Not determined

In another experiment, the antibacterial activity of the peptides according to the invention having a guanidinated N-terminus against the following pathogenic bacteria strains of the gram-positive bacterium *S. aureus* and of *P. aeruginosa* was analyzed:

TABLE 6

Antimicrobial activity against various pathogenic strains of *S. aureus*, and *P. aeruginosa* strains. MIC values were determined in triplicate in 1/8 MHB in µg/mL.

| SEQ ID No. | | S. aureus DSM 6247 | P. aeruginosa PAO DSM 9644 | E. coli DSM 1103 |
|---|---|---|---|---|
| 84 | gu-ONNRPVYIPRPRPPHPRR-OH | 8 | 64 | 4 |
| 85 | gu-OWNRPVYIPRPRPPHPRL-OH | 16 | 16 | 4 |
| 86 | gu-ONNRPVYIPRPRRPHPRL-OH | 32 | 32 | 8 |
| 87 | gu-OWNRPVYIPRPRRPHPRL-OH | 16 | 8 | 8 |
| 88 | gu-ONNRPVYIPRPRRPHPRL-NH$_2$ | 16 | 16 | 8 |
| 89 | gu-OWNRPVYIPRPRRPHPRL-NH$_2$ | 8-16 | 4 | 8 |

Gu: N-Terminus contains a tetramethylguanidino group (N-guanido-ornithine)

Additional measurements produced the following results.

TABLE 7

Antimicrobial activity against various pathogenic strains. MIC values were determined in triplicate in 1/8 MHB in µg/mL.

| SEQ ID No. | Peptide Sequence | E. coli BL21A1 TSB | E. coli ATCC 25922 TSB | Salmonella e. TSB | K. pneumoniae DSM 681 TSB | P. aeruginosa DSM 9644 TSB | S. aureus DSM 6247 MHB |
|---|---|---|---|---|---|---|---|
| | | | | Diluted medium | | | |
| 92 | gu-ONNRPVYIPRPRPPHPRL-NH$_2$ | 1 | 2 | — | 2 | 8 | 8 |
| 89 | gu-OWNRPVYIPRPRRPHPRL-NH$_2$ | 8 | 16 | — | >64 | 8 | 2 |
| 93 | gu-ONNRPVYIPRPRPPHPRL-OH | 1 | 4 | — | 2 | 16 | 16-32 |
| 85 | gu-OWNRPVYIPRPRPPHPRL-OH | 2 | 4 | — | 2 | 8-16 | 4 |

TABLE 7-continued

Antimicrobial activity against various pathogenic strains.
MIC values were determined in triplicate in 1/8 MHB in µg/mL.

| SEQ ID No. | Peptide Sequence | E. coli BL21A1 TSB | E. coli ATCC 25922 TSB | Salmonella e. TSB | K. pneumoniae DSM 681 TSB | P. aeruginosa DSM 9644 TSB | S. aureus DSM 6247 MHB |
|---|---|---|---|---|---|---|---|
| 87 | gu-OWNRPVYIPRPRRPHPRL-OH | 8 | 8 | – | 4-8 | 8 | 4 |
| | | | | Normal Medium | | | |
| 92 | gu-ONNRPVYIPRPRPPHPRL-NH₂ | – | – | – | – | – | – |
| 89 | gu-OWNRPVYIPRPRRPHPRL-NH₂ | – | – | – | – | – | – |
| 93 | gu-ONNRPVYIPRPRPPHPRL-OH | – | – | – | – | – | – |
| 85 | gu-OWNRPVYIPRPRPPHPRL-OH | – | – | – | – | – | – |
| 87 | gu-OWNRPVYIPRPRRPHPRL-OH | – | – | – | – | – | – |

The serum stability of selected apidaecin derivatives was also measured. The results are shown in Table 8.

TABLE 8

Serum stability of apidaecin WR derivatives in 25% and 100% mouse serum.

| SEQ ID No. | Sequence* | t½ [min] 25% serum | t½ [min] 100% serum | Degradation Products |
|---|---|---|---|---|
| 92 | gu-ONNRPVYIPRPRPPHPRL-NH₂ | 15 ± 1 | | gu-O1-R17 |
| 89 | gu-OWNRPVYIPRPRRPHPRL-NH₂ | 16 ± 1 | | gu-O1-R17, gu-O1-R12 |
| 93 | gu-ONNRPVYIPRPRPPHPRL-OH | | 350 ± 34 | gu-O1-R17 |
| 85 | gu-OWNRPVYIPRPRPPHPRL-OH | | 237 ± 15 | gu-O1-R17, gu-O1-R16 |
| 87 | gu-OWNRPVYIPRPRRPHPRL-OH | | 0% after 2 hours | gu-O1-R12 (Api341 analogue) |

The following abbreviations are used in the description of the invention:
BOC tert.-butyloxy carbonyl
ᵗBu tert.-butylether
DCM dichloromethane
DMF dimethylformamide
eq. equivalents per mol, mol equivalents
Fmoc fluorenylmethoxycarbonyl
Guan guanidino group (at the N-terminus)
Hyp trans-4-hydroxyproline
HBTU 2-(1H-benzotriazol-1-yl)-1,1,3,3-tetramethyluronium-hexafluorophosphate
HOBt 1-hydroxybenzotriazole
M mol/l
MALDI-TOF matrix assisted laser desorption/ionization with time of flight analysis
MIC minimum inhibitory concentration
MS mass spectrometry
Mtt 4-methyltrityl
NHS N-hydroxysuccinimide
NMM N-methylmorpholine
O ornithine
OᵗBu tert.-butylester
PBS phospho-buffered saline
RP-HPLC reversed phase high performance liquid chromatography
RT room temperature
TCA trichloroacetic acid
TFA trifluoroacetic acid
Tris tris(hydroxymethyl)-aminomethane
TSB tryptic soy broth

CITED NON-PATENT LITERATURE

Barra, D., Simmaco, M., and Boman, H. G. (1998) Gene encoded peptide antibiotics and innate immunity. Do 'animacules' have defense budgets? FEBS Lett. 430: 130-134.
Boman, H. G. (1995) Peptide antibiotics and their role in innate immunity. Annu. Rev. Immunol. 13: 61-92.
Czihal P. et al. (2007) Int J Antimicrob Agents 29, p. 602.
Ellman, J., Mendel, D., Anthony-Cahill, S., Noren, C. J., Schultz, P. G. (1991) Biosynthetic method for introducing unnatural amino acids site-specifically into proteins. Meth. Enzymol. 202: 301-336.
Gobbo, M., Biondi, L., Filira, F. and Rocchi R. (2006) The interaction of cationic antimicrobial peptides with vesicles containing synthetic glycolipids as models of the outer membrane of gram-negative bacteria. J. Pept. Sci. 12: 132-9.
Hilpert K. and Hancock, R. E. (2007) Use of luminescent bacteria for rapid screening and characterization of short cationic antimicrobial peptides synthesized on cellulose using peptide array technology. Nat. Protoc. 2: 1652-60.
Li, W. F., Ma, G. X. and Zhou, X. X. (2006) Apidaecin-type peptides: biodiversity, structure-function relationships and mode of action. Peptides. 27: 2350-9.
Maeno, M., Taguchi, S. and Momose, H. (1993) Production of antibacterial peptide 'apidaecin' using the secretory expression system of Streptomyces. Biosci. Biotechnol. Biochem. 57: 1206-7.

Noren, C. J., Anthony-Cahill, S. J., Griffith, M. C. and Schultz, P. G. (1989) A general method for site-specific incorporation of unnatural amino acids into proteins. *Science* 244: 182-188.

Otvos, L., Jr., Bokonyi, K., Varga, I., Otvos, B. I., Hoffmann, R., Ertl, H. C. J., Wade, J. D., McManus, A. M., Craik, D. J. and Bulet, P. (2000) Insect peptides with improved protease-resistance protect mice against bacterial infection. *Protein Sci.* 9: 742-749.

Reineke, U., Volkmer-Engert, R. and Schneider-Mergener, J. (2001) Applications of peptide arrays prepared by the SPOT-technology. *Curr. Opin. Biotechnol.* 12: 59-64.

Wiegand, I., Hilpert, K. and Hancock, R. E. (2008) Agar and broth dilution methods to determine the minimal inhibitory concentration (MIC) of antimicrobial substances. *Nat. Protoc.* 163-75.

---

The invention claimed is:

1. A peptide for use as a medicament in the treatment of an infection with gram-positive bacteria comprising an amino acid sequence selected from the group consisting of SEQ ID NO: 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 50, 52, 54, 55, 56, 57, 58, 59, 60, 61, 62, 63, and 64.

2. A pharmaceutical composition comprising the peptide of claim 1.

3. A host cell comprising the peptide of claim 1.

4. A peptide-multimer comprising at least two peptides according to claim 1, wherein the at least two peptides are bound to each other through a linker peptide.

* * * * *